(12) United States Patent  
Palreddy et al.

(10) Patent No.: US 7,991,459 B2
(45) Date of Patent: Aug. 2, 2011

(54) METHOD FOR DEFINING SIGNAL TEMPLATES IN IMPLANTABLE CARDIAC DEVICES

(75) Inventors: Surekha Palreddy, Maplewood, MN (US); Jay A. Warren, San Juan Capistrano, CA (US); Alan H. Ostroff, San Clemente, CA (US)

(73) Assignee: Cameron Health, Inc., San Clemente, CA (US)

( * ) Notice: Subject to any disclaimer, the term of this patent is extended or adjusted under 35 U.S.C. 154(b) by 166 days.

(21) Appl. No.: 11/941,781

(22) Filed: Nov. 16, 2007

(65) Prior Publication Data

US 2008/0119748 A1    May 22, 2008

Related U.S. Application Data

(63) Continuation of application No. 10/999,853, filed on Nov. 29, 2004, now Pat. No. 7,376,458.

(51) Int. Cl.
*A61B 5/04* (2006.01)
(52) U.S. Cl. ...................................... 600/516
(58) Field of Classification Search .......... 600/509, 600/516
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,030,509 A | 6/1977 | Heilman et al. |
| 4,157,720 A | 6/1979 | Greatbatch |
| 4,164,946 A | 8/1979 | Langer |
| 4,170,992 A | 10/1979 | Dillman |
| 4,184,493 A | 1/1980 | Langer et al. |
| 4,191,942 A | 3/1980 | Long |
| 4,210,149 A | 7/1980 | Heilman et al. |
| RE30,387 E | 8/1980 | Denniston, III et al. |
| 4,223,678 A | 9/1980 | Langer et al. |
| 4,248,237 A | 2/1981 | Kenny |
| 4,254,775 A | 3/1981 | Langer |
| 4,291,707 A | 9/1981 | Heilman et al. |

(Continued)

FOREIGN PATENT DOCUMENTS

DE        298 01 807 U1     7/1998

(Continued)

OTHER PUBLICATIONS

Wikidoc. "ST Elevation Myocardial Infarction Electrocardiogram." May 1, 2009. Aug. 3, 2009 <http://www.wikidoc.org/index.php/ST_elevation_myocardial_infarction_electrocardiogram>.*

(Continued)

*Primary Examiner* — Mark W Bockelman
*Assistant Examiner* — Elizabeth K So
(74) *Attorney, Agent, or Firm* — Pramudji Law Group PLLC; Ari Pramudji; Mark Schroeder

(57) ABSTRACT

Template formation methods for use in implantable cardiac rhythm management devices. In an illustrative method, a signal is captured in an implanted cardiac rhythm management device, and parameters for analysis of the captured signal are then defined. Then, in the example, additional signals can be captured and used to either verify or discard the captured signal defined parameters. The template formation methods provide for creating a robust template to compare with sensed cardiac complexes. Devices and systems configured to perform template formation and verification methods are also shown.

18 Claims, 13 Drawing Sheets

U.S. PATENT DOCUMENTS

| | | |
|---|---|---|
| 4,300,567 A | 11/1981 | Kolenik et al. |
| 4,314,095 A | 2/1982 | Moore et al. |
| 4,375,817 A | 3/1983 | Engle et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,548,209 A | 10/1985 | Wielders et al. |
| 4,567,900 A | 2/1986 | Moore |
| 4,595,009 A | 6/1986 | Leinders |
| 4,602,637 A | 7/1986 | Elmqvist et al. |
| 4,603,705 A | 8/1986 | Speicher et al. |
| 4,693,253 A | 9/1987 | Adams |
| 4,727,877 A | 3/1988 | Kallok |
| 4,750,494 A | 6/1988 | King |
| 4,765,341 A | 8/1988 | Mower et al. |
| 4,768,512 A | 9/1988 | Imran |
| 4,800,883 A | 1/1989 | Winstrom |
| 4,830,005 A | 5/1989 | Woskow |
| 4,944,300 A | 7/1990 | Saksena |
| 5,044,374 A | 9/1991 | Lindemans et al. |
| 5,105,810 A | 4/1992 | Collins et al. |
| 5,105,826 A | 4/1992 | Smits et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,215,081 A | 6/1993 | Ostroff |
| 5,217,021 A | 6/1993 | Steinhaus et al. |
| 5,230,337 A | 7/1993 | Dahl et al. |
| 5,255,692 A | 10/1993 | Neubauer et al. |
| 5,261,400 A | 11/1993 | Bardy |
| 5,271,411 A | 12/1993 | Ripley et al. |
| 5,273,049 A | 12/1993 | Steinhaus et al. |
| 5,300,106 A | 4/1994 | Dahl et al. |
| 5,313,953 A | 5/1994 | Yomtov et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,693 A | 7/1995 | Schroeppel |
| 5,439,485 A | 8/1995 | Mar et al. |
| 5,447,521 A | 9/1995 | Anderson et al. |
| 5,476,503 A | 12/1995 | Yang |
| 5,486,199 A | 1/1996 | Kim et al. |
| 5,509,923 A | 4/1996 | Middleman et al. |
| 5,509,928 A | 4/1996 | Acken |
| 5,522,852 A | 6/1996 | White et al. |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,607,455 A | 3/1997 | Armstrong |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,319 A | 8/1997 | Kroll |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,766,226 A | 6/1998 | Pedersen |
| 5,776,169 A | 7/1998 | Schroeppel |
| 5,779,645 A | 7/1998 | Olson et al. |
| 5,814,090 A | 9/1998 | Latterell et al. |
| 5,827,197 A | 10/1998 | Bocek et al. |
| 5,827,326 A | 10/1998 | Kroll et al. |
| 5,836,976 A | 11/1998 | Min et al. |
| 5,843,132 A | 12/1998 | Ilvento |
| 5,891,047 A * | 4/1999 | Lander et al. ................. 600/516 |
| 5,895,414 A | 4/1999 | Sanchez-Zambrano |
| 5,904,705 A | 5/1999 | Kroll et al. |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 5,957,956 A | 9/1999 | Kroll et al. |
| 5,991,657 A | 11/1999 | Kim |
| 6,014,586 A | 1/2000 | Weinberg et al. |
| 6,026,325 A | 2/2000 | Weinberg et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,093,173 A | 7/2000 | Balceta et al. |
| 6,095,987 A | 8/2000 | Shmulewitz et al. |
| H1905 H | 10/2000 | Hill |
| 6,128,531 A | 10/2000 | Campbell-Smith |
| 6,144,866 A | 11/2000 | Miesel et al. |
| 6,144,879 A | 11/2000 | Gray |
| 6,148,230 A | 11/2000 | KenKnight |
| 6,185,450 B1 | 2/2001 | Seguine et al. |
| 6,266,567 B1 | 7/2001 | Ishikawa et al. |
| 6,278,894 B1 | 8/2001 | Salo et al. |
| 6,280,462 B1 | 8/2001 | Hauser et al. |
| 6,308,095 B1 | 10/2001 | Hsu et al. |
| 6,334,071 B1 | 12/2001 | Lu |
| 6,345,198 B1 | 2/2002 | Mouchawar et al. |
| 6,377,844 B1 | 4/2002 | Graen |
| 6,397,100 B2 | 5/2002 | Stadler et al. |
| 6,411,844 B1 | 6/2002 | Kroll et al. |
| 6,493,579 B1 | 12/2002 | Gilkerson et al. |
| 6,493,584 B1 | 12/2002 | Lu |
| 6,516,225 B1 | 2/2003 | Florio |
| 6,567,691 B1 | 5/2003 | Stadler |
| 6,574,505 B1 | 6/2003 | Warren |
| 6,625,490 B1 | 9/2003 | McClure et al. |
| 6,647,292 B1 | 11/2003 | Bardy et al. |
| 6,684,100 B1 | 1/2004 | Sweeney et al. |
| 6,687,540 B2 | 2/2004 | Marcovecchio |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,865,417 B2 | 3/2005 | Rissmann et al. |
| 6,866,044 B2 | 3/2005 | Bardy et al. |
| 6,889,079 B2 | 5/2005 | Bocek et al. |
| 6,980,856 B2 | 12/2005 | Sullivan et al. |
| 6,996,434 B2 | 2/2006 | Marcovecchio et al. |
| 7,027,856 B2 | 4/2006 | Zhou et al. |
| 7,027,858 B2 | 4/2006 | Cao et al. |
| 7,031,764 B2 | 4/2006 | Schwartz et al. |
| 7,062,315 B2 | 6/2006 | Koyrakh et al. |
| 7,085,599 B2 | 8/2006 | Kim et al. |
| 7,162,301 B2 | 1/2007 | Kim et al. |
| 7,184,815 B2 | 2/2007 | Kim et al. |
| 7,184,818 B2 | 2/2007 | Kim et al. |
| 7,191,004 B2 | 3/2007 | Kim et al. |
| 2001/0027330 A1 | 10/2001 | Sullivan et al. |
| 2002/0049474 A1 | 4/2002 | Marcovecchio et al. |
| 2002/0183637 A1 | 12/2002 | Kim et al. |
| 2003/0013978 A1 * | 1/2003 | Schlegel et al. ................ 600/509 |

| | | | |
|---|---|---|---|
| 2004/0176694 | A1 | 9/2004 | Kim et al. |
| 2004/0254611 | A1 | 12/2004 | Palreddy et al. |
| 2004/0254613 | A1 | 12/2004 | Ostroff et al. |
| 2005/0049644 | A1 | 3/2005 | Warren et al. |
| 2005/0131476 | A1 | 6/2005 | Kim et al. |
| 2005/0131478 | A1 | 6/2005 | Kim et al. |
| 2005/0149125 | A1 | 7/2005 | Kim et al. |
| 2005/0234358 | A1 | 10/2005 | Cao et al. |
| 2005/0234359 | A1 | 10/2005 | Cao et al. |
| 2006/0074331 | A1 | 4/2006 | Kim et al. |
| 2006/0079796 | A1 | 4/2006 | Marcovecchio et al. |
| 2006/0167364 | A1 | 7/2006 | Houben |

FOREIGN PATENT DOCUMENTS

| | | |
|---|---|---|
| EP | 0 095 727 A1 | 12/1983 |
| EP | 0 316 616 A2 | 5/1989 |
| EP | 0 347 353 A1 | 12/1989 |
| EP | 0 316 616 A3 | 6/1992 |
| EP | 0 518 599 A2 | 12/1992 |
| EP | 0 517 494 A3 | 3/1993 |
| EP | 0 627 237 A1 | 12/1994 |
| EP | 0 641 573 A2 | 3/1995 |
| EP | 0 677 301 A1 | 10/1995 |
| EP | 0 517 494 B1 | 9/1996 |
| EP | 0 586 858 B1 | 3/1997 |
| EP | 0 641 573 A3 | 6/1997 |
| EP | 0 518 599 B1 | 9/1997 |
| EP | 0 536 873 B1 | 9/1997 |
| EP | 0 917 887 A1 | 5/1999 |
| EP | 0 923 130 A1 | 6/1999 |
| EP | 1 000 634 A1 | 5/2000 |
| WO | 93/19809 A1 | 10/1993 |
| WO | 97/29802 A2 | 8/1997 |
| WO | 98/25349 A1 | 6/1998 |
| WO | 99/03534 A1 | 1/1999 |
| WO | 99/37362 A1 | 7/1999 |
| WO | 99/53991 A1 | 10/1999 |
| WO | 00/41766 A1 | 7/2000 |
| WO | 00/50120 A1 | 8/2000 |
| WO | 01/43649 A1 | 6/2001 |
| WO | 01/56166 A2 | 8/2001 |
| WO | 02/22208 A2 | 3/2002 |
| WO | 02/24275 A2 | 3/2002 |
| WO | 02/24275 A3 | 5/2002 |
| WO | 02/22208 A3 | 6/2002 |
| WO | 02/43802 A2 | 6/2002 |
| WO | 2002-043802 A2 | 6/2002 |
| WO | 2002-043802 A3 | 8/2002 |
| WO | 02/068046 A1 | 9/2002 |
| WO | 2002-043802 A4 | 10/2002 |
| WO | 03/018121 A2 | 3/2003 |

OTHER PUBLICATIONS

Throne, et al.; "A Comparison of Four New Time-Domain Techniques for Discriminating Monomorphic Ventricular Tachycardia from Sinus Rhythm Using Ventricular Waveform Morphology"; IEEE Transactions on Biomedical Engineering; Jun. 1991; vol. 38, No. 6, pp. 561-570.

Bardy, et al.; "Multicenter Experience with a Pectoral Unipolar Implantable Cardioverter-Defibrillator"; JACC; Aug. 1996; vol. 28, No. 2, pp. 400-410.

Friedman, et al.; "Implantable Defibrillators In Children: From Whence to Shock"; Journal of Cardiovascular Electrophysiology; Mar. 2001; vol. 12, No. 3, pp. 361-362.

Ge, et al.; "Cardiac Arrhythmia Classification Using Autoregressive Modeling"; BioMedical Engineering OnLine, http://www.biomedical-engineeringonline.com; Nov. 13, 2002, 12 pages.

Gradaus, et al.; "Nonthoracotomy Implantable Cardioverter Defibrillator Placement in Children: Use of Subcutaneous Array Leads and Abdominally Placed Implantable Cardioverter Defibrillators in Children"; Journal of Cardiovascular Electrophysiology; Mar. 2001; vol. 12, No. 3, pp. 356-360.

Higgins, et al.; "The First Year Experience with the Dual Chamber ICD"; PACE; Jan. 2000; vol. 23, pp. 18-25.

Mirowski, et al.; "Automatic Detection and Defibrillation of Lethal Arrhythmias—A New Concept"; JAMA; Jul. 27, 1970; vol. 213, No. 4, pp. 615-616.

Olson, et al.; "Onset and Stability for Ventricular Tachyarrhythmia Detection in an Implantable Pacer-Cardioverter-Defibrillator"; IEEE; 1987, pp. 167-170.

Schuder; "Completely Implanted Defibrillator"; JAMA; Nov. 9, 1970; vol. 214, No. 6, p. 1123.

Schuder, et al.; "Experimental Ventricular Defibrillation with an Automatic and Completely Implanted System"; Trans. Amer. Soc. Artif. Int. Organs; 1970; vol. XVI, pp. 207-212.

Schuder; "The Role of an Engineering Oriented Medical Research Group in Developing Improved Methods and Devices for Achieving Ventricular Defibrillation: The University of Missouri Experience"; PACE; Jan. 1993; vol. 16, pp. 95-124.

Schuder, et al.; "Standby Implanted Defibrillators"; Arch Intern. Med; Feb. 1971; vol. 127, p. 317.

Schuder, et al.; "Transthoracic Ventricular Difibrillation in the Dog with Truncated and Untruncated Exponential Stimuli"; IEEE Transactions on Bio-Medical Engineering; Nov. 1971; vol. BME-18, No. 6, pp. 410-415.

Schwacke, et al.; "Komplikationen mit Sonden bei 340 Patienten mit einem Implantierbaren Kardioverter/Defibrillator"; Z Kardiol; 1999; vol. 88, No. 8, pp. 559-565.

Tietze et al., "Halbleiter-Schaltungstechnik"; © Springer-Verlag (Berlin,Germany); 1991; pp. 784-786.

Valenzuela, et al.; "Outcomes of Rapid Defibrillation by Security Officers After Cardiac Arrest in Casinos"; The New England Journal of Medicine; Oct. 26, 2000; vol. 343, No. 17, pp. 1206-1209.

Walters, et al.; "Analog to Digital Conversion Techniques in Implantable Devices"; Annual International Conference of the IEEE Engineering in Medicine and Biology Society; 1991; vol. 13, No. 4, pp. 1674-1676.

Swerdlow et al.; "Advanced ICD Troubleshooting: Part I"; Pacing and Clinical Electrophysiology; Jan. 9, 2006.

* cited by examiner

METHOD FOR DEFINING SIGNAL TEMPLATES IN IMPLANTABLE CARDIAC DEVICES

RELATED APPLICATIONS

This application is a Continuation of U.S. patent application Ser. No. 10/999,853, filed Nov. 29, 2004, now U.S. Pat. No. 7,376,458, and titled METHOD FOR DEFINING SIGNAL TEMPLATES IN IMPLANTABLE CARDIAC DEVICES, the disclosure of which is incorporated herein by reference.

The present invention is related to U.S. patent application Ser. No. 10/999,274, filed Nov. 29, 2004, now U.S. Pat. No. 7,477,935, and titled METHOD AND APPARATUS FOR BEAT ALIGNMENT AND COMPARISON, the disclosure of which is incorporated herein by reference.

FIELD

The present invention relates generally to implantable cardiac systems that detect, sense and classify cardiac signals. More particularly, the present invention relates to implantable medical devices that generate a template from which the medical device can make comparisons to a patient's normal cardiac complex.

BACKGROUND

Implantable cardiac rhythm management devices are an effective treatment in managing irregular cardiac rhythms in particular patients. Implantable cardiac rhythm management devices are capable of recognizing and treating arrhythmias with a variety of therapies. To effectively deliver these therapies, however, cardiac rhythm management devices must first accurately sense and classify an episode.

In order to apply the proper therapy in responding to an episode, some cardiac rhythm management devices compare sensed cardiac signals to a previously stored "template" representing normal sinus rhythm (NSR) or other "template" frequently intended to represent the patient's NSR. This stored NSR template must accurately characterize a patient's true NSR in order to be used in a process that properly identifies potentially fatal deviations from normal cardiac activity.

Problems arise when the cardiac rhythm management device inaccurately compares a sensed cardiac complex to a stored NSR template, and as a result, misclassifies the sensed cardiac complex. The severity of this problem escalates if the cardiac rhythm management device inappropriately delivers therapy due to the misclassification. In illustration, when a particular group of sensed complexes are erroneously compared to a stored template because of an improper alignment to the template, a cardiac rhythm management device may mistakenly classify these sensed complexes as a mismatch and even possibly as a tachyarrhythmia.

For the reasons stated above, and for other reasons stated below, which will become apparent to those skilled in the art upon reading and understanding the present specification, there is a need in the art for providing a reliable system to generate templates for comparison with sensed cardiac events to accurately classify and, if indicated, treat the cardiac rhythm a patient is experiencing.

SUMMARY

The present invention is directed toward template formation methods for use in cardiac rhythm management devices. The template formation methods of the present invention provide for creating a robust template to compare with sensed cardiac complexes. In an illustrative embodiment, the present invention is used to form templates having a template data set and template alignment parameters for use in aligning captured signals with the template data set prior to comparing the template data set to captured signals.

An illustrative embodiment includes a method of cardiac signal analysis comprising sensing a first cardiac event, configuring template parameters for analysis of the first cardiac event, defining a first sensed signal for the first cardiac event using the template parameters, sensing a second cardiac event, defining a second sensed signal for the second cardiac event using the template parameters, and comparing the second sensed signal to the first sensed signal to determine whether the first sensed signal and template parameters are suitable for defining a cardiac event template. In another embodiment, the illustrative method is performed such that the step of configuring template parameters includes selecting a rule for identifying a fiducial point, wherein the rule is selected from among a set of rules, the rule is selected in light of the characteristics of the first cardiac event, and the rule for identifying a fiducial point becomes one of the template parameters. In a further embodiment, the step of configuring template parameters further includes selecting a number of samples of the first sensed signal around the fiducial point, wherein the configuration of samples around the fiducial point becomes one of the template parameters. The step of selecting a number of samples may include identifying the start and end of a cardiac event. For some embodiments, the set of rules includes an amplitude rule related to the relative amplitudes of peaks in the sensed signal, and a location rule related to the location of a peak in the sensed signal.

Another illustrative embodiment includes a method of cardiac signal analysis including forming a template for cardiac event comparisons, the step of forming a template comprising sensing a first cardiac event, identifying a first fiducial point in the first cardiac event using a set of rules, sensing a second cardiac event, identifying a second fiducial point in the second cardiac event using the set of rules, determining whether the first fiducial point and second fiducial point were identified using the same rule, and, if not, discarding the first cardiac event.

In yet another embodiment, a method of cardiac signal analysis comprises sampling a signal using electrodes implanted in a patient's torso for capturing cardiac signals, defining a first sensing window around a first fiducial point to capture a QRS segment, observing the definition of the first sensing window to create template parameters, defining a second sensing window around a second fiducial point using the template parameters, and comparing data in the first sensing window to data in the second sensing window to verify whether to define a valid template using the template parameters.

Another embodiment includes a method of cardiac signal template formation comprising receiving a first cardiac signal from implanted electrodes, selecting a fiducial point in the first cardiac signal, forming a template around the fiducial point, and verifying the template by receiving a second cardiac signal and using the template to compare the second cardiac signal to the first cardiac signal.

DETAILED DESCRIPTION OF THE DRAWINGS

The following detailed description should be read with reference to the drawings, in which like elements in different drawings are numbered identically. The drawings, which are not necessarily to scale, depict selected embodiments and are not intended to limit the scope of the invention. Those skilled in the art will recognize that many of the examples provided have suitable alternatives that may be utilized.

The present invention is generally related to implantable cardiac treatment systems that provide therapy for patients who are experiencing particular arrhythmias. The present invention is directed toward detection architectures for use in cardiac rhythm devices. In particular, the present invention is suited for implantable cardiac treatment systems capable of detecting and treating harmful arrhythmias. Although the detection architecture is intended primarily for use in an implantable medical device that provides defibrillation therapy, the invention is also applicable to cardiac rhythm devices (including external devices) directed toward anti-tachyarrhythmia pacing (ATP) therapy, pacing or other cardiac stimulation techniques, and other cardiac rhythm devices capable of performing a combination of therapies to treat rhythm disorders.

To date, implantable cardiac treatment systems have been either epicardial systems or transvenous systems. For example, transvenous systems can be implanted generally as shown in FIG. 1B. However, as further explained herein, the present invention is also adapted to function with a subcutaneous implantable cardiac treatment system as shown in FIG. 1A.

Figure 1A:
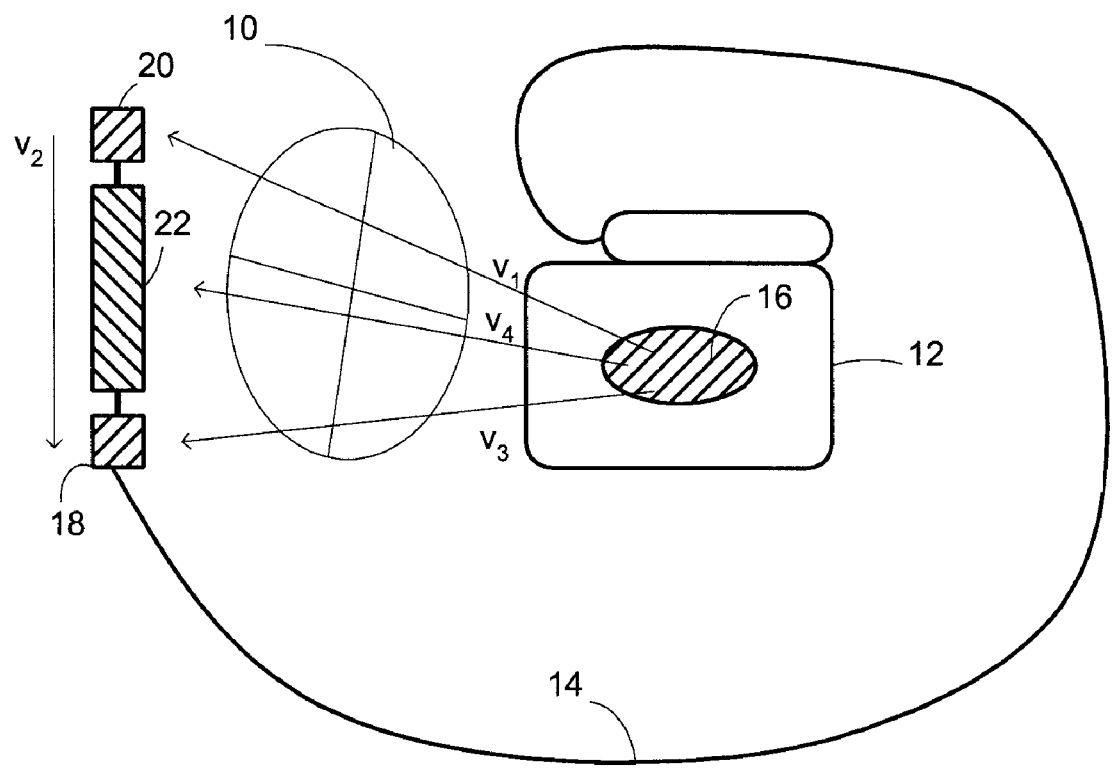
FIGS. 1A-1B illustrate, respectively, representative subcutaneous and intravenous implantable cardiac treatment systems.
Figure 1B:
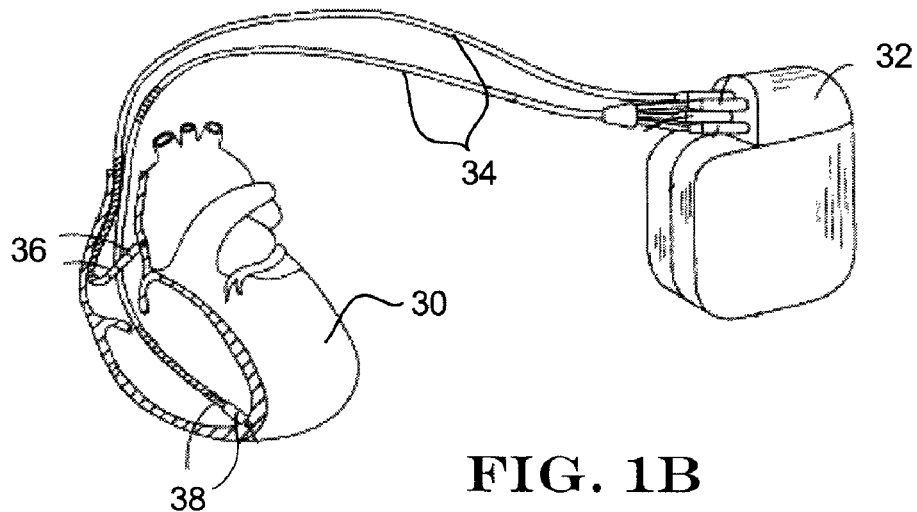

FIG. 1A illustrates a subcutaneously placed implantable cardiac treatment system, in particular, an implantable cardioverter/defibrillator (ICD) system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647,292 and 6,721,597, the disclosures of which are both incorporated herein by reference. By subcutaneous placement, it is meant that electrode placement does not require insertion of an electrode into a heart chamber, in or on the heart muscle, or the patient's vasculature.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature.

Figure 2:
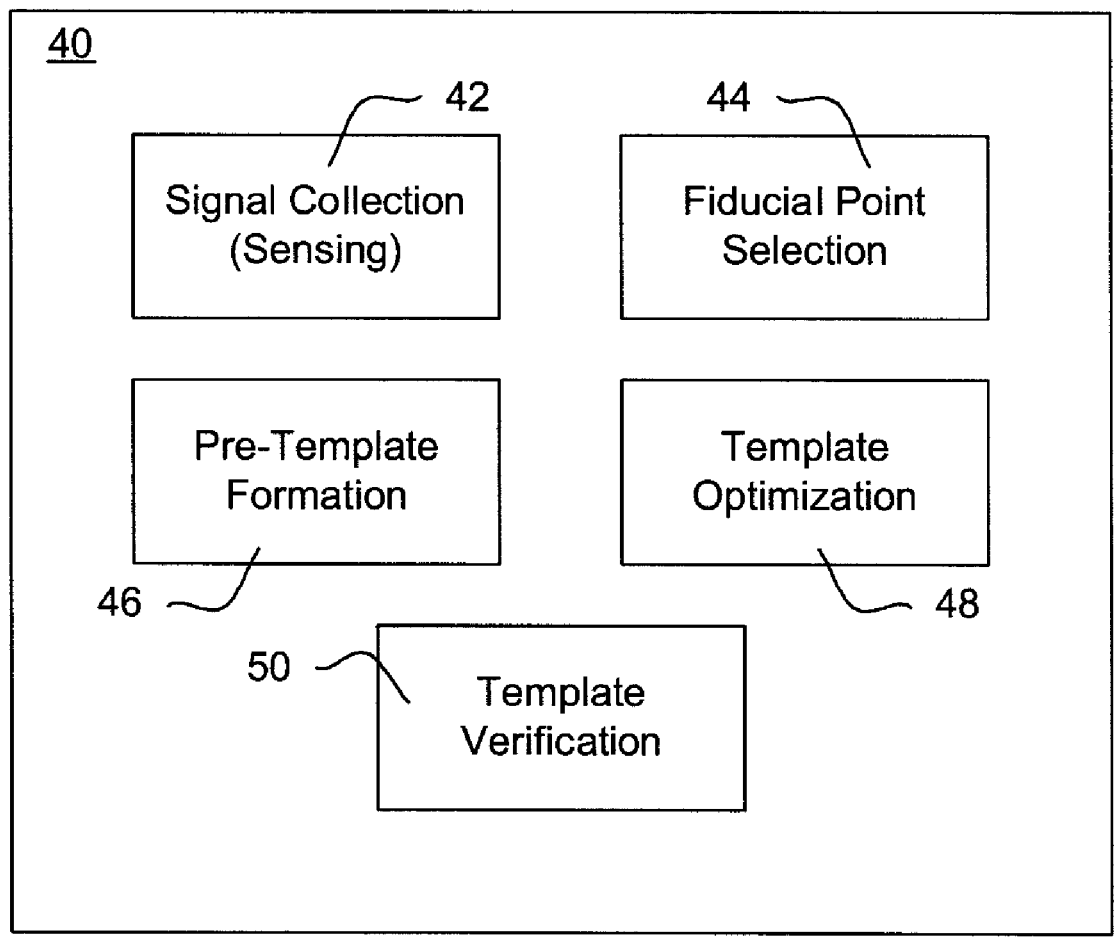
FIG. 2 depicts a template formation system in accordance with an illustrative embodiment of the present invention.

FIG. 2 depicts a template formation system 40 in accordance with an illustrative embodiment of the present invention. The template formation system 40 can be used to create and store multiple static and/or dynamic templates. Static templates are cardiac complexes that are captured previously in time and stored for reference by the device. Alternatively, dynamic templates are cardiac complexes that are continuously or periodically captured and/or updated.

The template formation system 40 of the present invention generally comprises a multi-stage data analysis—signal collection 42, fiducial point selection 44, pre-template formation 46, template optimization 48, and template verification 50. Sections of the multi-stage data analysis, however, may operate autonomously, as will be discussed in detail below. As such, a particular process in the template formation system 40 may be bypassed or may function independently in the device's overall detection architecture.

The system, in an illustrative embodiment, not only identifies NSR signals for comparison to sensed events, it also defines and re-defines the sensing parameters (for example, fiducial point selection, window size, and/or window/fiducial point alignment). These signals and parameters can then be used for making comparisons with a sensed cardiac signal to determine whether the signal is NSR.

The processes within the template formation system 40 may additionally create or modify a template to accommodate for morphological changes in the patient's cardiac complex. For example, the ultimately formed template may be continually updated to adapt to certain morphological changes in the sensed cardiac complex. As such, the template formation system 40 of the present invention is adaptive and this adaptive characteristic may be automated.

The template formation system 40 is initiated by collecting a cardiac signal 42. The cardiac signal may be collected using any suitable capture method. This sensed cardiac complex is then processed for proper alignment. A method for repetitive and reliable alignment of a collected signal enhances the accuracy when comparing sensed signals to a stored template. In some embodiments, the step of collecting the cardiac signal 42 may include a signal certification process such as that illustrated in co-pending U.S. patent application Ser. No. 10/858,598, filed Jun. 1, 2004, now U.S. Pat. No. 7,248,921, entitled METHOD AND DEVICES FOR PERFORMING CARDIAC WAVEFORM APPRAISAL, and the disclosure of which is incorporated herein by reference.

In several embodiments of the present invention, a fiducial point for alignment is generally established using a preferred peak of the sensed cardiac complex. The fiducial point may be selected manually for each patient, or alternatively, the fiducial point may be selected using a rule-based method. In preferred embodiments, the fiducial point is selected by analyzing the repetitive nature of peaks on "n" consecutive complexes. In one embodiment of the present invention, the fiducial point selection process 44 is based on the results of the most recently sensed cardiac complex and the three (3) cardiac complexes previous to the most recently sensed complex. Alternative embodiments may base the fiducial point selection process 44 on the repetitive nature of as many as 20 consecutive complexes to as few as an ongoing beat to beat determination.

A preferred fiducial point selection process 44 implements a set of rules to choose the most appropriate peak for alignment in a cardiac complex. In preferred embodiments, the fiducial point selection process 44 is based on an amplitude rule and a location rule. Additionally, due to the nature of the fiducial point selection process 44 rules, while the R-wave will often be chosen since it is frequently associated as the most striking phase deflection observed in a cardiac complex, the R-wave is not necessarily selected as the fiducial point for alignment in any given cardiac complex.

The first rule used by the illustrative fiducial point selection process 44 is the amplitude rule. This rule sets the fiducial point on the peak (either positive or negative) of the QRS cardiac complex having the greatest relative amplitude. The amplitude rule is set forth as:

If the positive peak amplitude >2 times the negative peak amplitude, then fiducial point selection is on the peak of the positive phase deflection—"positive amplitude";

If the negative peak amplitude >2 times the positive peak amplitude, then fiducial point selection is on the peak of the negative phase deflection—"negative amplitude";

If neither the positive peak nor the negative peak satisfies the amplitude rule, then the location rule, set forth below, controls.

Figure 3:
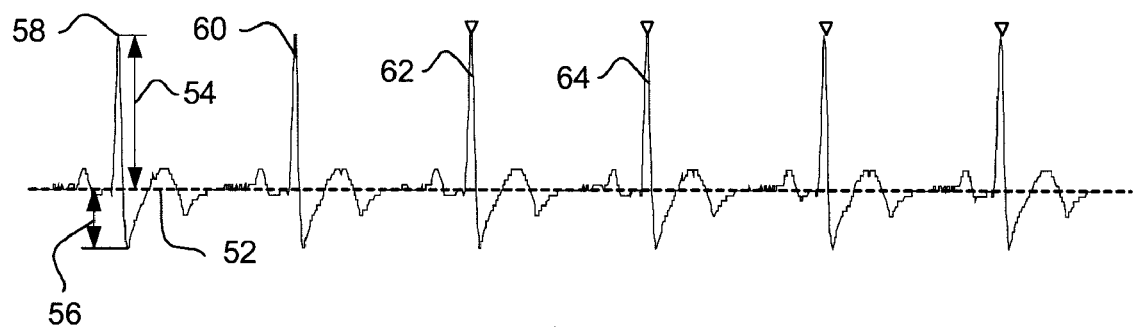
FIG. 3 shows selection of a positive peak of a cardiac complex based on an amplitude rule of a fiducial point selection process.

The relative amplitudes for the positive and negative peaks are measured from the patient's isoelectric line 52—illustrated in FIG. 3. The isoelectric line represents a signal lacking significant detected phase deflection, i.e. a detected signal level that does not indicate cardiac activity and provides a baseline for signal analysis. The fiducial point selection process 44 then determines the largest positive and negative phase deflections from the isoelectric line 52. In the present example, the amplitude of the largest positive phase deflection is shown as 54. Similarly, the amplitude of the largest negative phase deflection is shown as 56. The relative amplitudes of both the positive phase deflection 54 and negative phase deflection 56 are then assessed. If the relative amplitude of the positive phase deflection is greater than two times the relative amplitude of the negative phase deflection, the fiducial point selection is suggested to be on the positive amplitude peak.

In the present example, the fiducial point selection process is established by the repetitive nature of four consecutive cardiac complexes. Cardiac complexes 58, 60, 62 and 64 each demonstrate a positive peak amplitude greater than two times (2×) its corresponding negative peak amplitude. After the fourth consecutive cardiac complex 64, the fiducial point selection process establishes the positive peak as the fiducial point for alignment based on the amplitude rule. The triangles shown in FIG. 3 represent points where the amplitude rule has been met in four consecutive complexes. Additionally, each triangle signifies an established fiducial point for template alignment.

Figure 4:
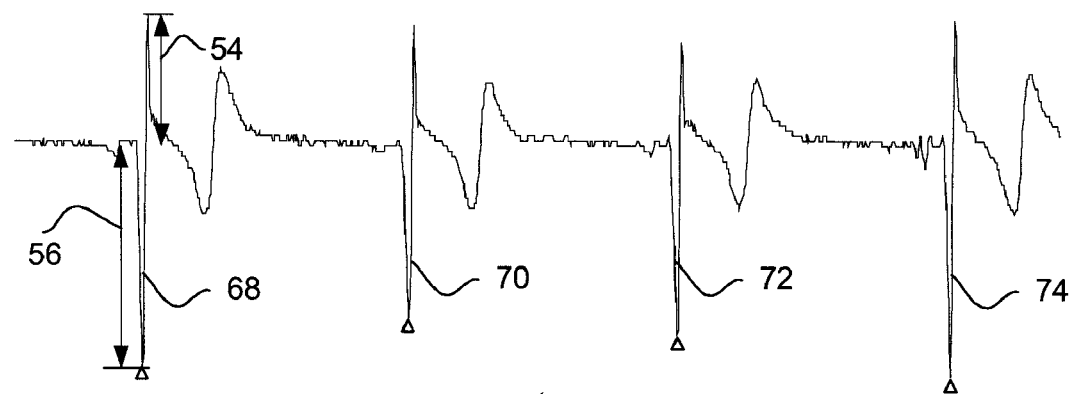
FIG. 4 shows selection of a negative peak of a cardiac complex based on an amplitude rule of a fiducial point selection process.

FIG. 4 shows fiducial point selection of a negative peak based on the amplitude rule. In the present example, the fiducial point selection process is established by the repetitive nature of a sensed cardiac complex and the previous three sensed cardiac complexes (four consecutive cardiac complexes). Cardiac complexes 68, 70, 72 and 74 each demonstrate a negative peak amplitude greater than two times (2×) its corresponding positive peak amplitude. Specifically, the amplitude of the largest negative phase deflection 56 is assessed to be two times the relative amplitudes of the positive phase deflection 54. After the fourth consecutive cardiac complex 74, the fiducial point selection process establishes the negative peak as the fiducial point for alignment based on the amplitude rule. The triangles shown in FIG. 4 represents a point where the amplitude rule has been met for four consecutive complexes. Additionally, each triangle signifies an established fiducial point for template alignment.

The second rule used by the illustrative peak alignment process is the location rule. This rule is premised on setting the fiducial point on the peak of the first significant phase deflection (either positive or negative) occurring in time within the ventricular cardiac complex. In certain embodiments, the location rule is considered when the amplitude rule cannot be established. Alternate embodiments utilize the location rule without deference to the amplitude rule. The location rule is set forth as:

If a significant positive phase deflection precedes a significant negative phase deflection in a cardiac complex, then fiducial point selection is on the peak of the positive phase deflection—"positive location";

If a significant negative phase deflection precedes a significant positive phase deflection in a cardiac complex, then fiducial point selection is on the peak of the negative phase deflection—"negative location".

Figure 5:
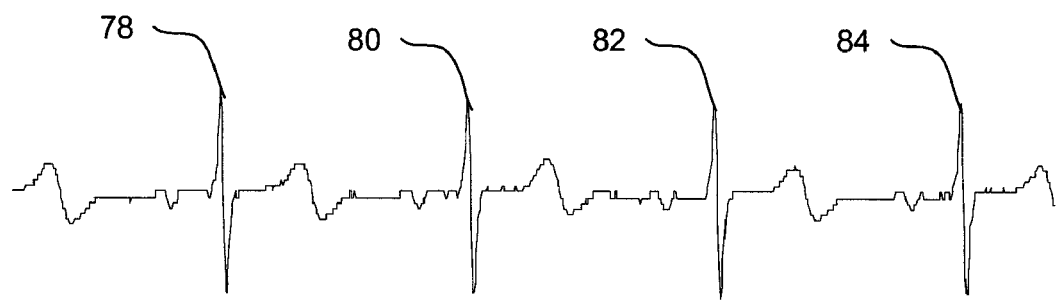
FIG. 5 shows selection of a positive peak of a cardiac complex based on a location rule of a fiducial point selection process.

FIG. 5 shows an illustrative fiducial point selection of a positive peak based on the location rule. In the present example, the fiducial point selection process is established by the repetitive nature of four consecutive cardiac complexes. Cardiac complexes 78, 80, 82 and 84 each show a significant positive phase deflection before a significant negative phase deflection in the cardiac complex. After the fourth consecutive cardiac complex 84, the fiducial point selection process establishes the peak of the positive phase deflection as the fiducial point for alignment based on the location rule. The triangles shown in FIG. 5 represent points where the location rule has been met in four consecutive complexes. Additionally, each triangle signifies an established fiducial point for template alignment.

Figure 6:
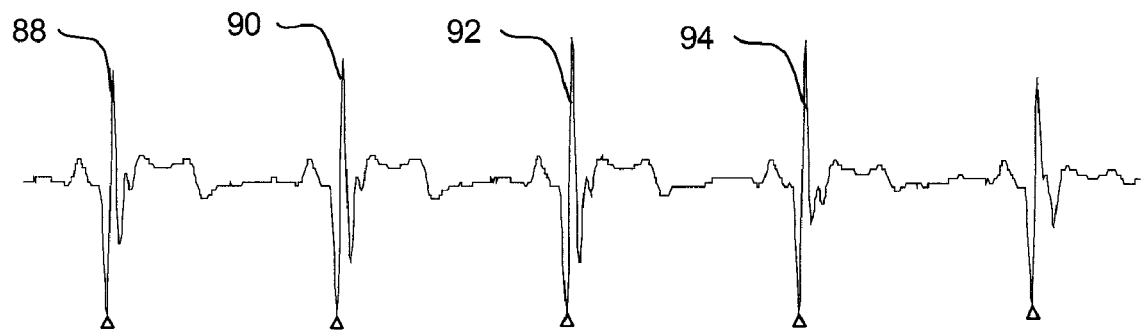
FIG. 6 shows selection of a negative peak of a cardiac complex based on a location rule of a fiducial point selection process.

FIG. 6 shows an illustrative fiducial point selection of a negative peak based on the location rule. The fiducial point selection process in FIG. 6 is established by the repetitive nature of four consecutive cardiac complexes. Cardiac complexes 88, 90, 92 and 94 each show a significant negative phase deflection before a significant positive phase deflection in the cardiac complex. After the fourth consecutive cardiac complex 94, the fiducial point selection process establishes the peak of the negative phase deflection as the fiducial point for alignment based on the location rule. The triangles shown in FIG. 6 represent a point where the location rule has been met for four consecutive complexes. Additionally, each triangle signifies an established fiducial point for template alignment.

In certain embodiments where the fiducial point selection process requires more than one cardiac complex to establish a fiducial point, the process may require each of the cardiac complexes assessed to adhere to the same rule (amplitude or location) before establishing a fiducial point for alignment. More particularly, each cardiac complex analyzed and used for establishing a fiducial point must adhere to the same one of the four possible rule bases: positive amplitude, negative amplitude, positive location, or negative amplitude.

In alternative embodiments, the fiducial point selection process may require all of the cardiac complexes assessed to establish the same fiducial point (i.e., the same positive peak) regardless of which rule was used. In an illustrative embodiment, the fiducial point selection process is established by the repetitive nature of three consecutive cardiac complexes. Two of the three cardiac complexes may establish the fiducial point on the positive peak using the positive amplitude rule base. The remaining cardiac complex may establish the same fiducial point on the complex's positive peak, however, using the positive location rule and not the amplitude rule. While not using the same rule, all three cardiac complexes indicate the same fiducial point, and as such, are indicated for submission to template verification, as referred to in FIG. 2.

Figure 7:
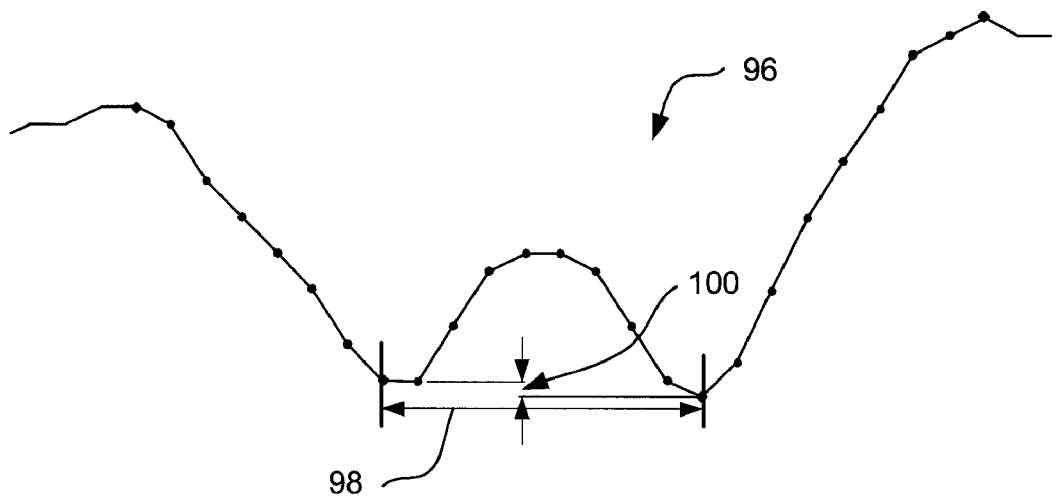
FIG. 7 depicts a cardiac signal possessing a notch in the QRS segment.

In certain circumstances, a notch is observed in the cardiac signal's QRS segment. FIG. 7 depicts a cardiac signal possessing a notch 96 in the QRS segment. A notch in a cardiac signal normally fails to affect the fiducial point selection process. This is observed because a predominant peak usually exists amongst the peaks forming the notch. Thus, the fiducial point selection process will generally select the predominant peak. In instances where one peak does not stand out over the other peak (as is depicted in FIG. 7), or when the predominant peak frequently changes from cardiac complex to cardiac complex, a potential for confusion in the fiducial point selection process may arise. In embodiments possessing such problematic notch segments, a notch analysis process may be used to assure the proper fiducial point selection for alignment.

In an illustrative notch analysis process, a notch is presumed to exist if the distance (in time) between the two peaks 98 is more than approximately 20 msec and/or if the difference in peak amplitudes 100 is less than approximately 115 µV. These values may vary in several embodiments depending upon the placement and design of sensing electrodes, as well as the expected characteristics of notched QRS peaks for a given patient. If these conditions are not met, it is presumed that a predominant peak does exist, that the fiducial point selection process will identify the predominant peak, and so the illustrative notch analysis process is skipped. However, if these conditions are met, then the cardiac signal is presumed to possess a notch requiring further analysis for proper fiducial point selection.

The illustrative notch analysis process identifies the peaks in the signal, and determines which peak has been initially identified as the fiducial point. If the first peak occurring in time is identified as the fiducial point, then the notch analysis is complete. If the second peak occurring in time is identified as the fiducial point, then the notch analysis process forces the fiducial point onto the first peak of the notch occurring in time.

Figure 8:
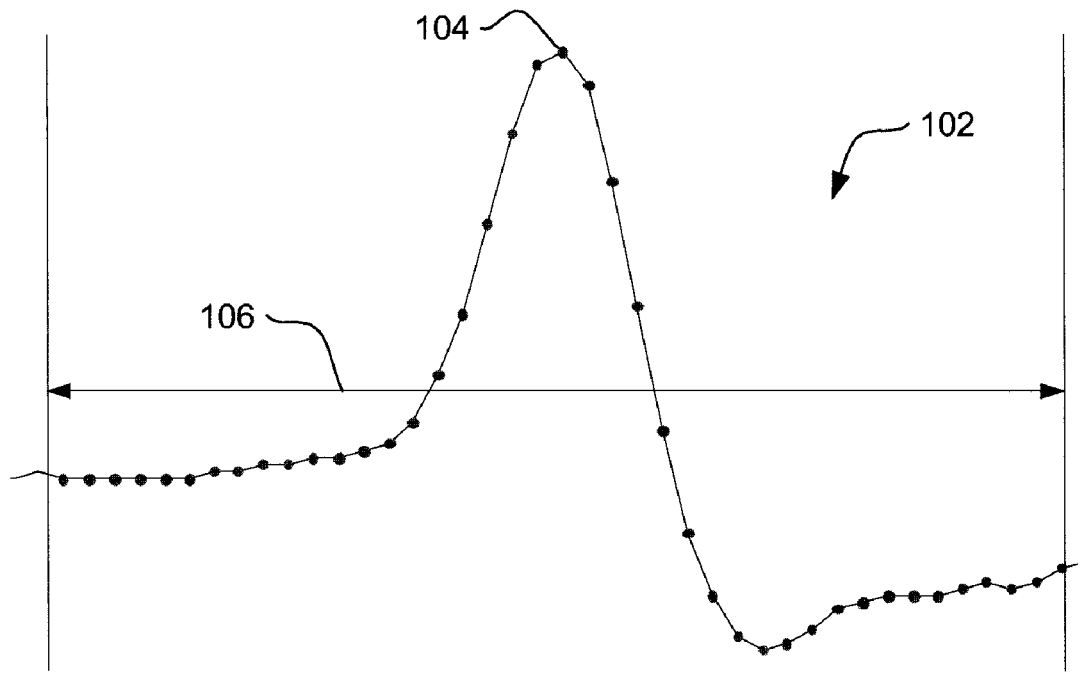
FIG. 8 shows a pre-template template window.

Once the fiducial point is selected, the pre-template is then formed. FIG. 8 is an illustrative embodiment of a pre-template 102. The pre-template 102 is populated with a number of samples taken at a sampling frequency which form a pre-template data set. In the illustrative embodiment, the disposition of the pre-template data set within the pre-template is determined by template alignment parameters including the fiducial point selection explained above and the placement and masking steps further discussed below.

In an illustrative embodiment, the fiducial point 104 is placed at the center of the pre-template 102. In preferred embodiments, a number of samples 'n' are established to the left of the fiducial point 104, and 'n' samples are also established to the right of the fiducial point 104. For example, some embodiments of the present invention utilize forty-one (41) samples sampled at 256 Hz, corresponding to approximately 160 msec. In an illustrative embodiment, twenty (20) samples are established to the left of the fiducial point 104 and another twenty (20) samples are established to the right of the fiducial point 104. The forty-one (41) samples form a pre-template window 106 in which the relevant portion of a cardiac signal will be analyzed. In alternative embodiments, the number of samples 'n' populated on either side of the center of the pre-template 102 may differ.

From this initially formed pre-template window 106, the boundaries of the cardiac complex's QRS segment are sought. FIG. 8 shows a pre-template window 106 that includes a QRS segment as well as extraneous portions of a sensed cardiac signal. In this instance, it is desired to optimize the formed pre-template 102 by narrowing the pre-template window 106 to comprise mostly the QRS segment and reduce extraneous portions of the cardiac signal. The first step in this process is to identify the beginning and end of the QRS segment.

In one embodiment of the present invention, the observation of monotonic segments is used to estimate the beginning and end of the QRS segment. A monotonic segment is a signal segment of consecutive samples in which the sensed amplitude changes in the same direction or stays the same. For example, a series of consecutive samples in which each successive sample is greater than or equal to (in amplitude) the previous sample would be an increasing monotonic segment. Similarly, a series of consecutive samples in which each successive sample is less than or equal to (in amplitude) the previous sample would be a decreasing monotonic segment. One method for observing monotonic segments is by determining the zero crossing points of the first derivative of the cardiac complex signal.

Figure 9:
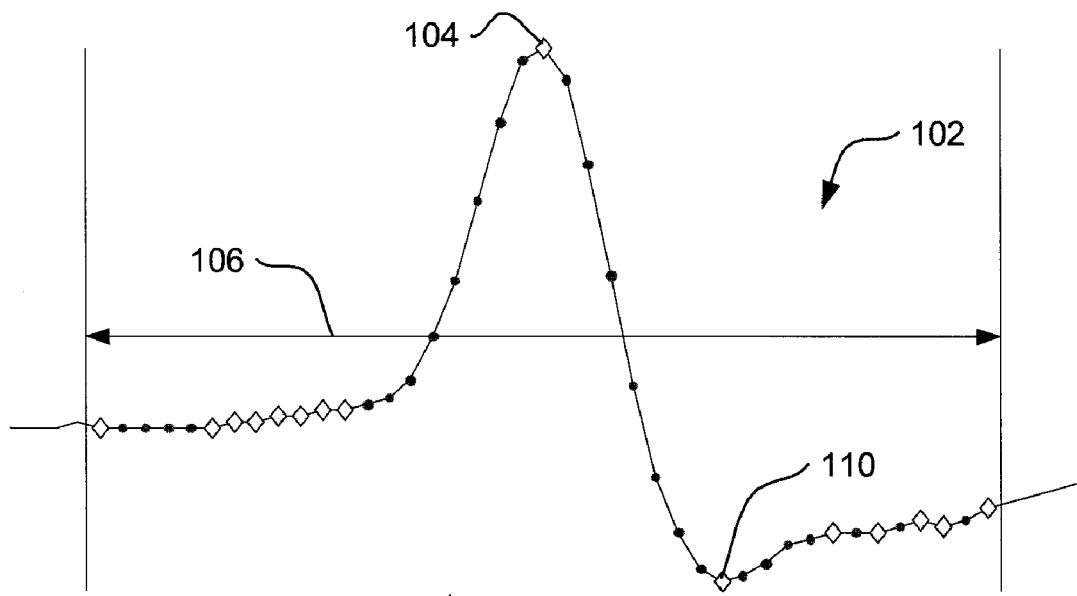
FIG. 9 shows the pre-template template window depicted in FIG. 8 after the monotonic segments are identified in the cardiac complex.

In this embodiment, an arithmetic operation is performed on the initial pre-template 102 to identify the cardiac complex's monotonic segments—as indicated by the zero crossing points of the first derivative of the cardiac complex signal. FIG. 9 shows the pre-template window 106 depicted in FIG. 8 after all of the monotonic segments are identified in the cardiac complex. Each diamond indicates the beginning/end of a monotonic segment. An arithmetic operation then identifies the largest monotonic segment (in terms of change of amplitude) in the initial pre-template 102 before the fiducial point 104. This sample is noted as "QRS begin" 108. The arithmetic operation further identifies the largest monotonic segment (in terms of change of amplitude) in the initial pre-template 102 after the fiducial point 104. This sample is noted as "QRS end" 110. QRS begin and QRS end estimate the boundaries for the cardiac complex's QRS segment in this embodiment.

Figure 10:
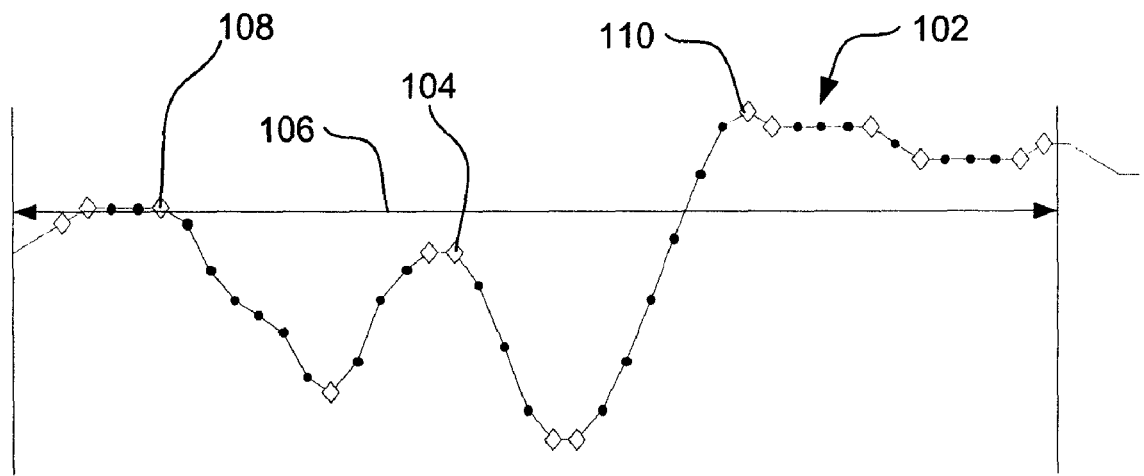
FIG. 10 depicts a cardiac signal having a notch within the cardiac signal's QRS segment.

The use of monotonic segments is further useful for eliminating errors in calculating QRS segment length with cardiac complexes having a notch in their QRS segment. FIG. 10 illustrates a cardiac complex possessing a notch. Since the arithmetic operation of the illustrative embodiment identifies the largest monotonic segment (in amplitude) in the initial pre-template 102 before the fiducial point 104 and after the fiducial point 104, most notches will not affect the algorithm's ability to find the desired QRS begin and QRS end. As depicted in FIG. 10, the relative monotonic segment amplitudes within the notch are smaller than the amplitudes of the monotonic segments at either end of the QRS segment. Therefore, the notch generally does not affect the estimated measurement of the QRS segment.

Alternative methods known in the art may also be utilized to estimate the beginning and end of the cardiac complex's QRS segment. The use of monotonic segments to estimate the QRS segment is merely illustrative, and various embodiments of present invention are not limited to this particular aspect of the illustrative embodiment.

After the QRS segment has been identified, the pre-template 102 is then optimized for performance—process 46 in FIG. 2. Optimization includes, but is not limited to, masking the pre-template window 106 to include the most relevant samples in the cardiac complex, as well as offset adjustment.

Figure 11:
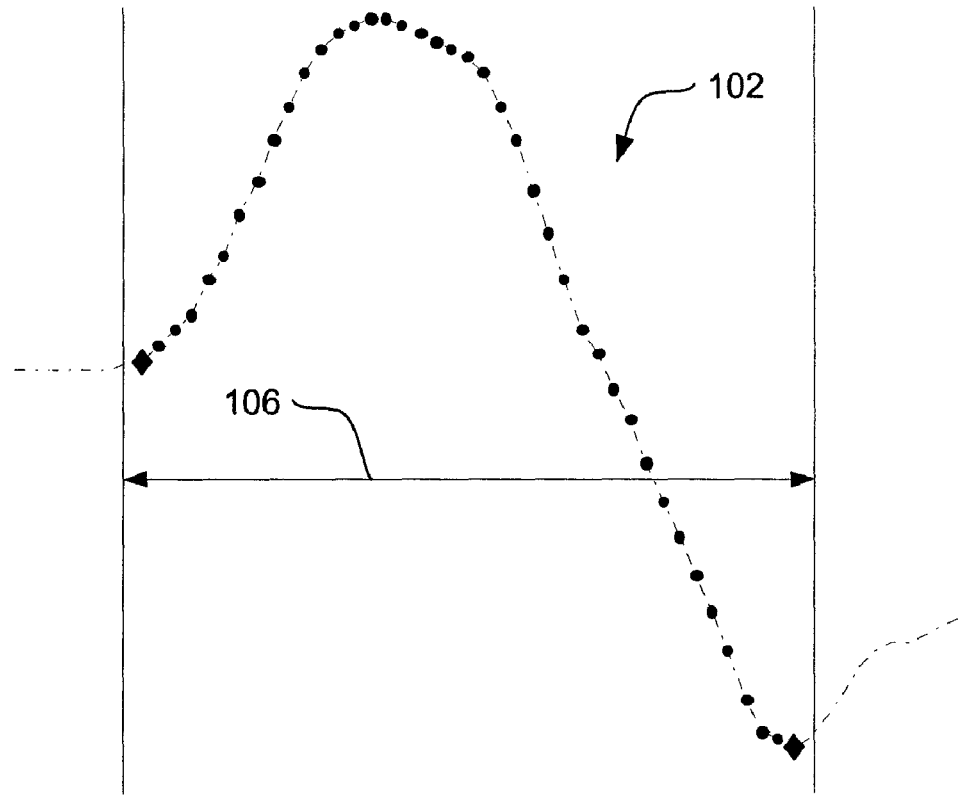
FIG. 11 depicts the template window for a patient having a wide QRS.

One method for template optimization is to narrow or mask the pre-template window 106 to include only those samples indicative of the QRS segment. In patients with wide QRS segments, optimization by removal of some samples is not indicated. For example, in the above illustrative embodiment, if a patient has a QRS segment longer than 160 msec (or 41 samples), the patient's QRS segment exceeds the initially formed pre-template window 106. Thus, the patient's identified QRS begin 108 is the first sample within the pre-template window 106 and the identified QRS end 110 is the last sample within the pre-template window 106, even though the patient's actual QRS segment may extend beyond the confines of the formed pre-template window 106. An example of a wide QRS segment that exceeds the size of the pre-template window 106 is shown in FIG. 11. Masking the pre-template window 106 is not indicated in these instances.

Figure 12:
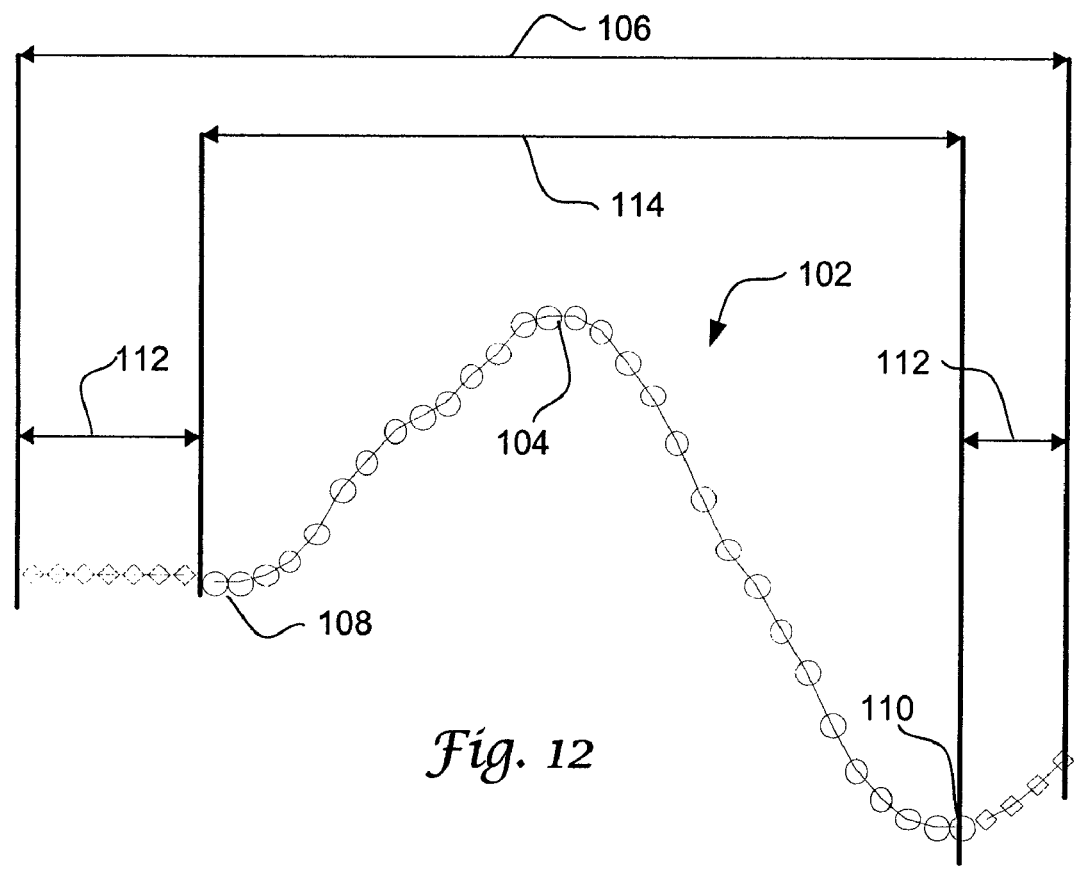
FIG. 12 shows a cardiac complex having a QRS segment that is capable of having its pre-template template window narrowed by masking.
Figure 13:
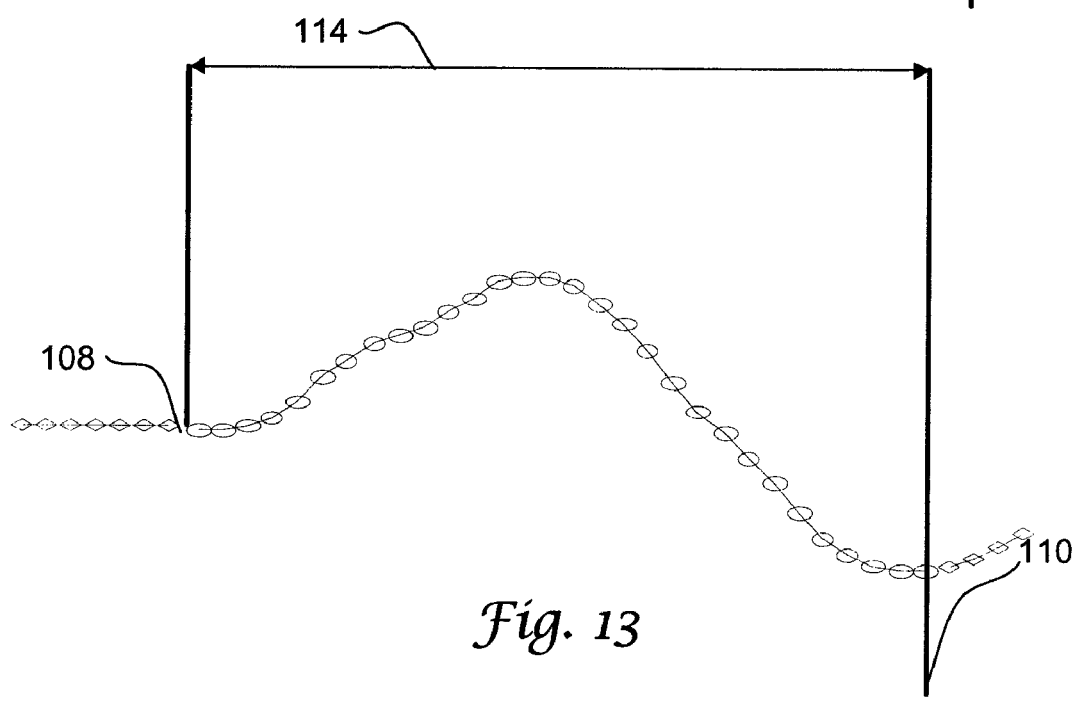
FIG. 13 depicts the observed template window after adjusting the template window's bounds.

In contrast, the pre-template window 106 may be masked when the QRS segment is less than the pre-template's window 106. For example, and as depicted in FIG. 12, suppose a patient's QRS begin 108 is at the fourth sample within the pre-template window 106. Similarly, suppose the patient's QRS end 110 occurs on the thirty-fifth sample within the pre-template window 106. Thus, the patient's QRS segment is thirty-two (32) samples long. The other nine (9) samples included in the original pre-template window 106 are generally not useful for analysis, and may introduce undesired effects if included in the final template. Therefore, the bounds of the pre-template 102 may be masked to form a masked pre-template window 114 that only includes the actual QRS segment—between QRS begin 108 and QRS end 110. In this example, the pre-template window 106 would be masked to the 32 samples representing the estimated QRS segment. Specifically, the pre-template bounds are masked so that the masked pretemplate window 114 begins on sample 4 and ends on sample 35, thereby eliminating extraneous samples 112 from the masked pre-template window 114. FIG. 13 depicts the observed masked pre-template window 114 after the masking process. Such narrowing or masking, while useful in some embodiments, is not required by the present invention.

If desired, a minimum duration for the masked pre-template window 114 may be defined. In one embodiment of the present invention, the minimum masked pre-template window 114 is approximately 100 msec (25 samples at 256 Hz).

Figure 14:
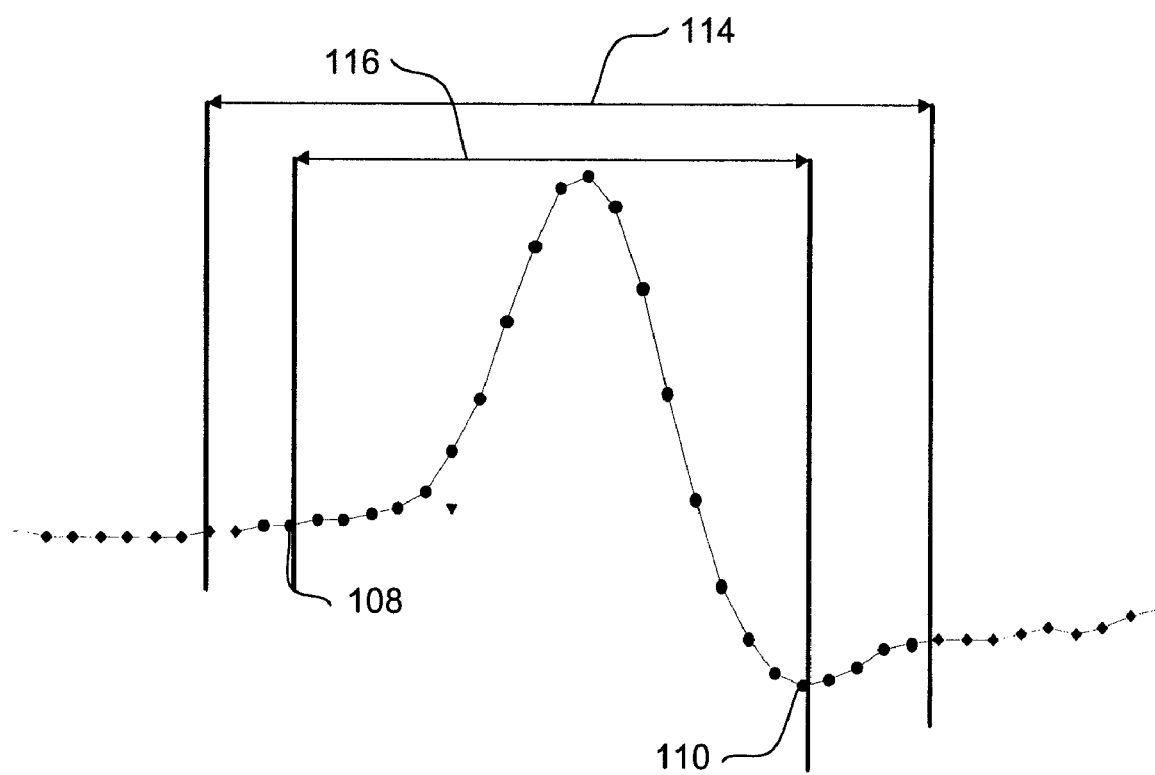
FIG. 14 shows a cardiac complex having a QRS segment width that is smaller than the acceptable minimum template window.

In patients having narrow QRS segments (less than approximately 100 msec), the allowable masked pre-template window 114 may still include some extraneous samples with the QRS segment for these patients. For example, as depicted in FIG. 14, if the QRS begin 108 is on sample twelve (12) and the QRS end 110 occurs on sample twenty-nine (29), then the width of the QRS segment is eighteen (18) samples. This QRS segment width is smaller than the illustrative minimum for the masked pre-template window 114 of twenty-five (25) samples. To mask the QRS segment to the minimum boundary allowable, the difference is first calculated between the masked pre-template window's minimum (25 samples) and the estimated QRS segment width (eighteen (18) samples in this example). This difference is seven (7) samples. The difference is then split in half and added equally (or as equally as possible) to both sides of the estimated QRS segment length. Thus, the optimized masked pre-template window 114 in this example would include the actual QRS segment 116 with three (3) additional samples preceding the QRS begin 108 and four (4) additional samples following the QRS end 110.

Figure 15:
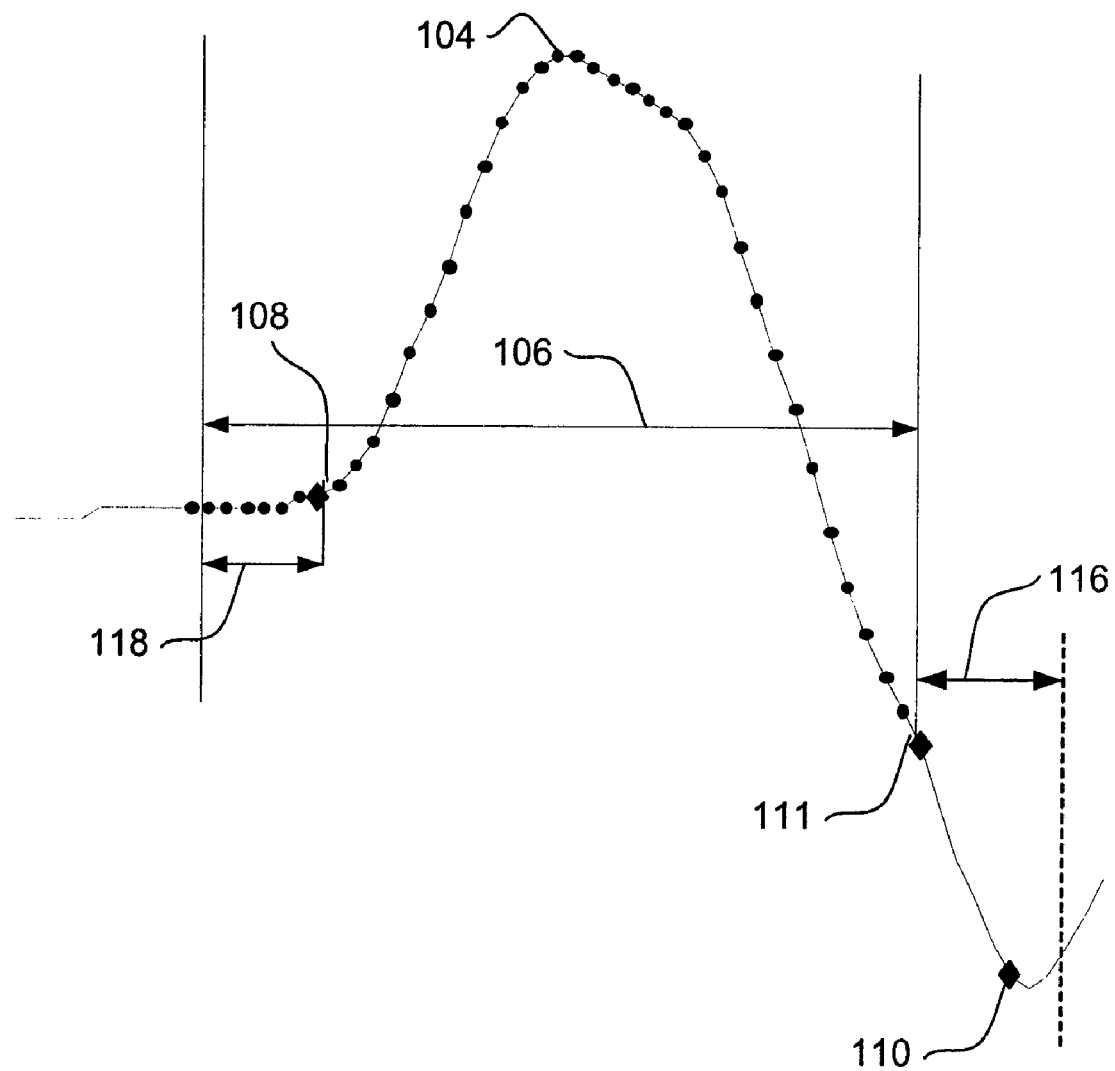
FIG. 15 illustrates a QRS segment that was not properly captured through the pre-template template window formation process.

There are other instances where the pre-template window 106 does not include the complete QRS segment. An example of such an instance is when the sample indicating the QRS begin 108 or QRS end 110 occurs on the first or last sample within the initially formed pre-template window 106. In some embodiments, this gives rise to an assumption that the actual QRS begin 108 or QRS end 110 is not accurately captured and that the actual QRS begin 108 or QRS end 110 occurs sometime outside the boundaries of the initially formed pre-template window 106. An example of a pre-template window 106 where the last sample within the pre-template window is also the QRS end 110 is depicted in FIG. 15. In FIG. 15, a pre-template window 106 is populated with samples 1 through 41. The first sample appears near the vertical axis midpoint of the template window. In contrast, the last sample (sample 41) appears near the bottom of the template window's vertical axis. As the samples move along the horizontal axis from sample 1, the samples gradually increase in height until reaching the QRS begin 108 for the cardiac complex segment. The remainder of the pre-template window 106 contains most, but not all, of the QRS segment. The remainder of the QRS segment not captured within the boundaries of the pre-template window 106 is shown as 116. In such an instance, the entire QRS segment was not properly captured through the pre-template window 106 formation process. Some embodiments of the present invention resolve this issue through an offset adjustment.

The offset adjustment process first identifies which side of the QRS segment was not properly captured. As described above and depicted in FIG. 15, the QRS begin 108 is sample eight (8) and the perceived QRS end 111 is sample forty-one (41). This generally indicates that the true QRS end 110 actually occurs at a point later in time and was not captured using the initial settings for forming the pre-template window 106. When it is indicated that the true QRS end 100 was not properly captured, a number of samples will precede the QRS begin 108. These leading samples are called the "residue" 118. In FIG. 15, the residue consists of the first seven (7) samples preceding the QRS begin 108. Since the samples constituting the residue 118 relay little information regarding the QRS segment itself, these samples may be discarded and replaced by samples that do represent the QRS segment but which were omitted through the initial pre-template window formation process. The process for shifting the pre-template window 106 in one direction is called offset. The effect of the offset process, in the present example, is to allow the pretemplate window 106 to start 'n' number of residue samples later to ensure that the true QRS end 110 is captured.

In a preferred embodiment, the sample representing the QRS begin 108 plus the immediately preceding sample (QRS begin −1), or the QRS end 110 plus the immediately following sample (QRS end +1), along with the samples therebetween, are retained. The remaining samples comprise the residue 118. In alternative embodiments, the QRS begin 108 or the QRS end 110, plus some 'n' number of samples preceding or following, is retained and the remaining samples comprises the residue 118. In yet alternative embodiments, just the QRS begin 108 or QRS end 110 is kept and the remaining samples are considered residue.

Figure 16:
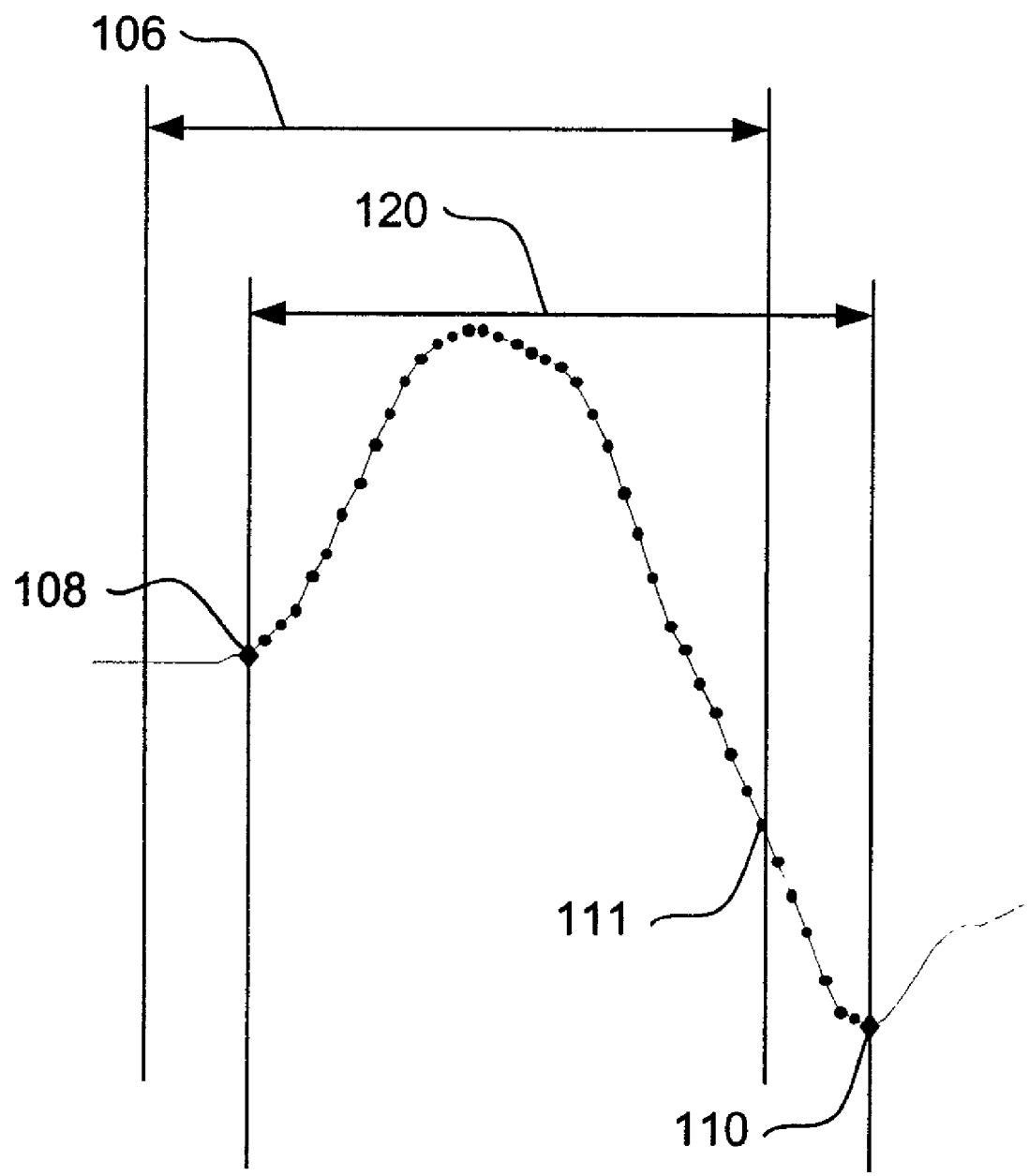
FIG. 16 shows the result of an offset adjustment process to the QRS segment captured in FIG. 15.

FIG. 16 illustrates the offset process on the cardiac complex depicted in FIG. 15. Specifically, FIG. 16 depicts the formation of an offset pre-template window 120 to recapture the cardiac complex's true QRS end 110. As described above, FIG. 15 shows that there are eight (8) residue samples 118 leading the QRS begin 108. These residue samples 118 are eliminated and QRS begin 108 is forced to be the first sample in a newly formed offset pre-template window 120. This adjustment is graphically depicted in FIG. 16. Thus, the offset pre-template window 120 starts at the QRS begin 108 and now ends eight (8) samples later than it initially did when the pre-template window 106 was initially formed. The result of this shift permits the newly formed offset pre-template window 120 to recapture the cardiac complex's true QRS end 110. Thus, the offset pre-template window 120 comprises the entire QRS segment including both the true QRS begin 108 and the true QRS end 110.

In preferred embodiments, after the offset adjustment process, the corrected template window is further optimized by masking the bounds of the offset template—as described above.

The parameters used in defining the optimized pre-template window are, in an illustrative example, described as the template parameters. The template parameters describe how the template data set is defined and aligned within the template. These parameters, including the manner of fiducial point selection, offset (if any) and masking (if any) provide template parameters indicating how the template can be used in making future comparisons. The template parameters may be used as described in copending U.S. patent application Ser. No. 10/999,274, filed Nov. 29, 2004, entitled METHOD AND APPARATUS FOR BEAT ALIGNMENT AND COMPARISON, and assigned to the assignee of the present invention; the disclosure of the application is also incorporated herein by reference. However, in the illustrative embodiment, prior to using the template (including its associated template parameters and template data set) for future comparisons to sensed signals, the template data set is verified for validity.

Figure 17:
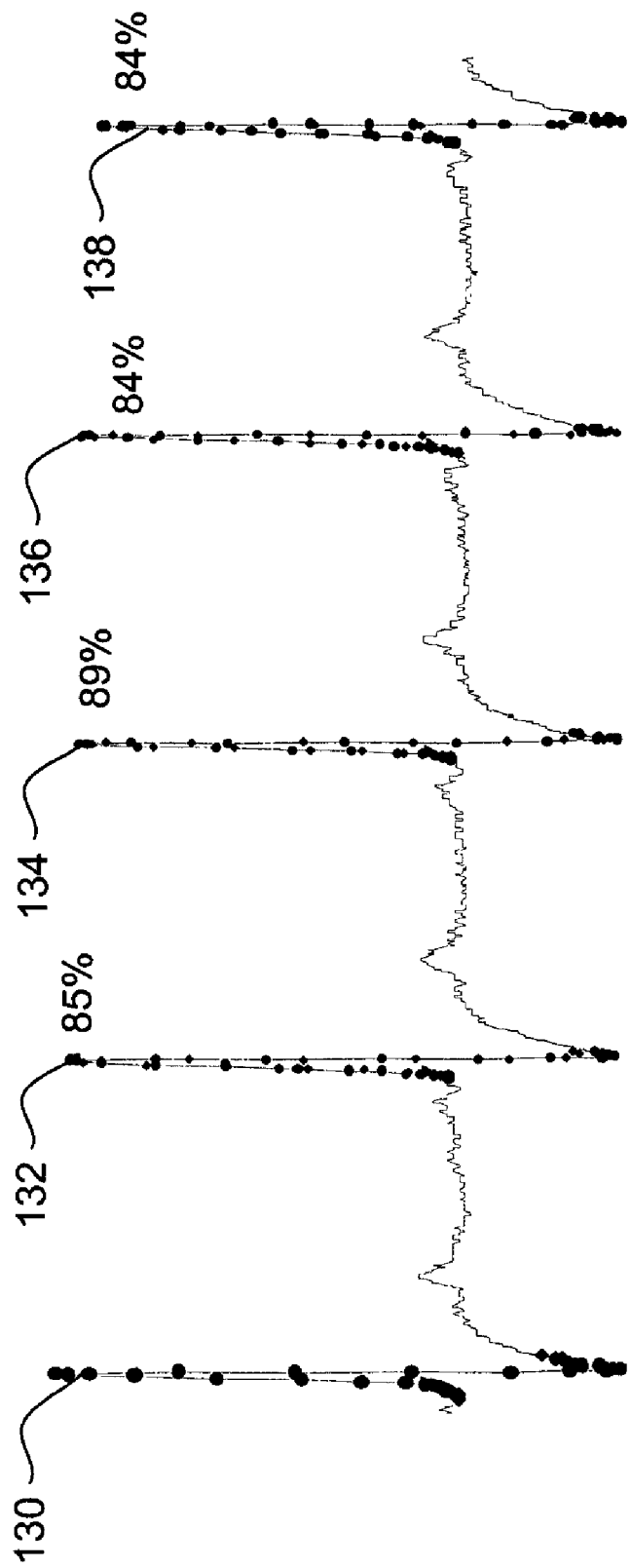
FIG. 17 illustrates a template verification process.

Once the pre-template is optimized by defining its sample window characteristics, including but not limited to masking and offset adjustment, the data in optimized pre-template is verified for its validity—process 50 in FIG. 2. The verification of optimized pre-template validity provides a check on both the template parameters and the template data set. In preferred embodiments, validity must be established before the optimized pre-template is stored as the final template, or as one template among several for use in comparing to subsequently sensed cardiac signals. FIG. 17 illustrates the template verification process 50 for an optimized pre-template.

The optimized pre-template 130 is initially stored in a buffer. The device then senses a subsequent cardiac complex 132 using the optimized parameters set for the optimized pre-template 130. Cardiac complex 132 is then compared to the stored optimized pre-template 130. In a preferred embodiment, an arithmetic operation similar to correlation is performed to determine the similarity between 130 and 132. An illustrative arithmetic operation includes correlation waveform analysis, which returns a result between −1 and 1, and which can be scaled using a number of linear, non-linear, and hybrid scaling methods as noted in co-pending U.S. application Ser. No. 10/856,084 filed May 27, 2004 entitled METHOD FOR DISCRIMINATING BETWEEN VENTRICULAR AND SUPRAVENTRICULAR ARRHYTHMIAS, and the disclosure of which is incorporated herein by reference.

In an illustrative embodiment, a correlation waveform analysis is performed and then scaled to a percentage value between 0-100%, with negative correlations given a 0%, and positive scores linearly scaled between 0-100%. If the similarity score between the subsequent cardiac complex 132 and the optimized pre-template 130 is greater than a specified threshold, the subsequent cardiac complex 132 is averaged with the optimized pre-template 130. In certain embodiments of the present invention, the threshold for comparison is specified at 80%. Alternative threshold levels may be set without deviating from the spirit and scope of the invention. Additionally, in certain embodiments, the cardiac complex that is compared to the optimized pre-template 130 is not averaged after comparison. If the similarity score does not surpass the specified threshold, then the optimized pre-template 130 is discarded and the entire template formation process is restarted.

In certain embodiments, if the comparison threshold value is exceeded, then the verification process is repeated with another incoming cardiac complex, for example cardiac complexes 134, 136 and 138. The device captures the cardiac complex 134 using the parameters set for the averaged optimized pre-template (130+132) and performs a further comparison between the cardiac complex 134 and the averaged optimized pre-template (130+132). Again, alternative embodiments may compare the newly sensed cardiac complex 134 to the initially stored optimized pre-template 130. In the present illustrative example, the comparison score between the cardiac complex 134 and the averaged optimized pre-template (130+132) is 85%. Since this score is greater than the comparison threshold of 80%, the verification process is continued.

The verification process is repeated at least this one additional time in some embodiments of the present invention. In a preferred embodiment, this process is iterated until four (4) consecutive cardiac complexes exceed the threshold level for comparison with either the initially stored optimized pre-template 130, or the averaged optimized pre-template (130+132+134+136). If at any time during the process the similarity score does not surpass the specified threshold, then the optimized pre-template is discarded and the template formation process is restarted in its entirety until a verified template is created.

The template is verified after completing the specified number of iterations for the verification process. In the present illustrative embodiment, the comparison scores to the averaged optimized pre-template for cardiac complexes 132, 134, 136 and 138 were 85%, 89%, 84% and 84%, respectively. Each of these comparison scores exceeded the comparison threshold set for the present example. Thus, the optimized pre-template is verified and the pre-template is considered the final template, thereby completing the template formation process. The formed template can then be used to observe and characterize incoming sensed cardiac signals.

Figure 18A:
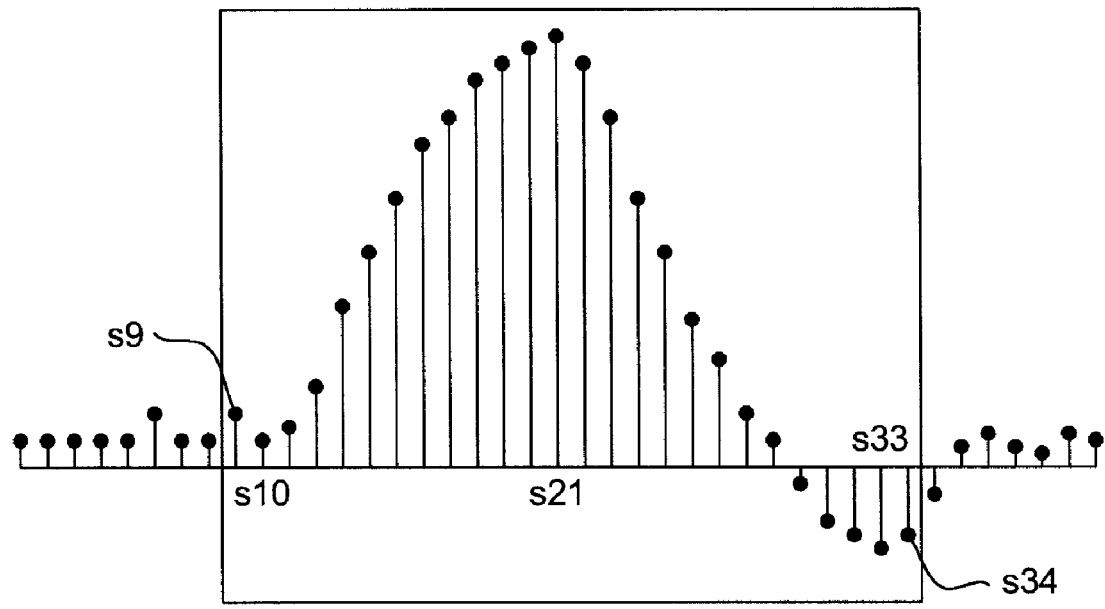
FIGS. 18A-18C further illustrate a template verification step.
Figure 18B:
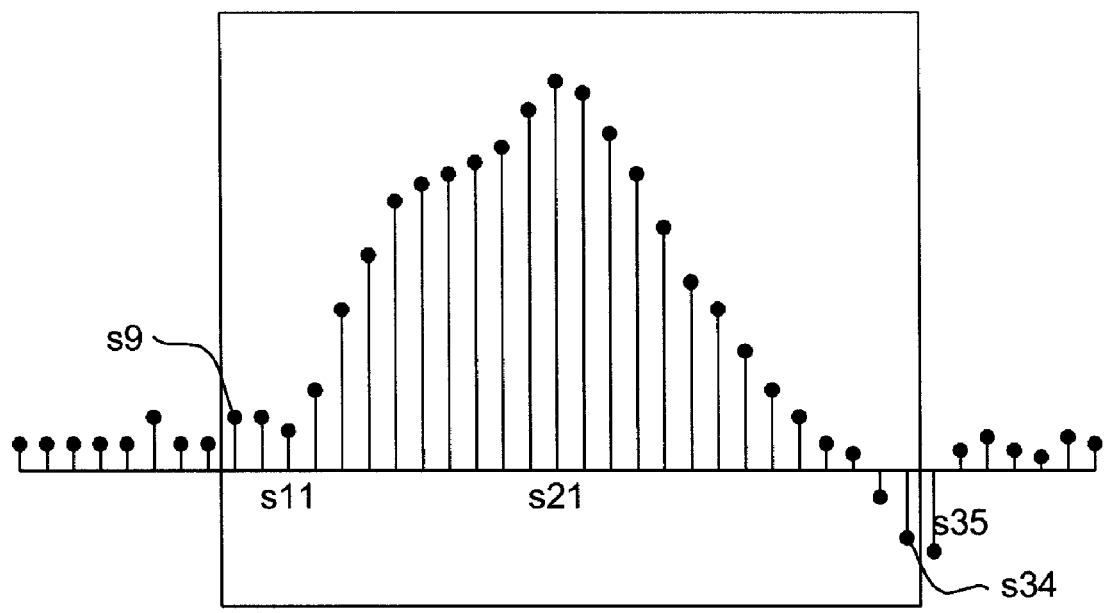
Figure 18C:
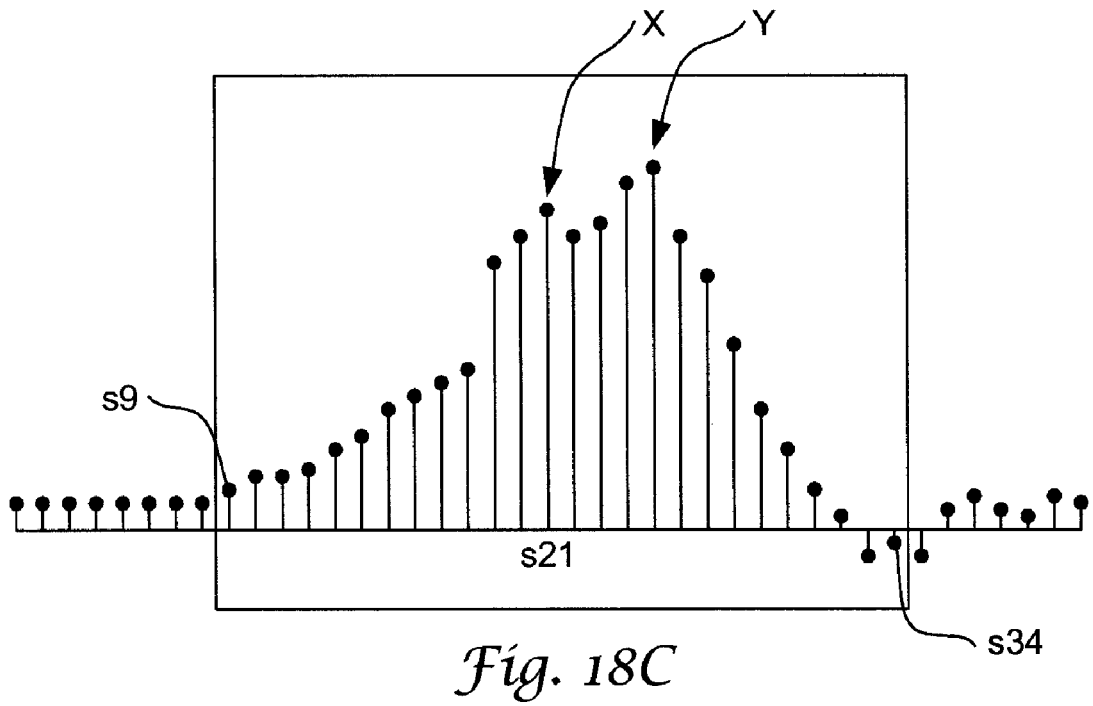

FIGS. 18A-18C further illustrate a template verification step. As shown in FIG. 18A, a sampled signal is placed into a pre-template template having a fiducial point which is defined using the amplitude rule. The fiducial point is placed as sample s21, with 20 samples on either side making up the pre-template template window. QRS start and end points are identified at s10 and s33, respectively. The signal and its parameters are referred to as an optimized pre-template. Next, the signal is masked using QRS +/−1 rules, such that the optimized pre-template is as shown by the box, extending from sample s9 to s34. The optimized pre-template is then stored until verified.

Turning to FIG. 18B, another sampled signal is captured and the optimized pre-template parameters from FIG. 18A are used to define the signal window. In particular, the amplitude rule is used to select a fiducial point and place it at sample s21, and the sample is masked to only include samples s9 to s34. As can be seen, the captured QRS segment in FIG. 19B is not accurately masked, as the QRS signal ends at s35, outside the signal window, and the QRS start occurs one sample later than would be desired. However, the overall shape generally resembles that of FIG. 18A, and a correlation of the two signals could be calculated to yield a score above a defined threshold such as 0.8 or 80% correlation. Thus the signal in FIG. 18B could be retained for averaging with that of FIG. 18A to further characterize the optimized pre-template. Alternatively, the data may not be averaged and the signal in the optimized pre-template of FIG. 18A used in further analysis. In another alternative, the verification provided by the signal in FIG. 18B could be defined as sufficient to store that of FIG. 18A as a template for comparison.

Turning to FIG. 18C, a third sampled signal is captured for comparison to the signal in 18A. The first step here is to identify the fiducial point. However, it can be seen that there are two positive peaks X and Y which are near one another. Neither peak qualifies for the amplitude rule, as each has nearly the same amplitude. Therefore the location rule would have to be used to select the fiducial point. In an illustrative embodiment, this fact alone would be enough to discard the signal and/or discard the template formed using the signal of FIG. 18A, as the same rule sets could not be used to define the fiducial point.

In other embodiments, the sampled signal of FIG. 18C may still be used for template verification even though a different fiducial point rule is used. Under such an embodiment, the signal from FIG. 18C may still cause rejection of the template formed using the signal shown in FIG. 18A. More particularly the signals in FIG. 18A and FIG. 18C are poorly correlated, as it can be seen that the signal to the left of the fiducial point s21 is lower, while the signal to the right of the fiducial point s21 is higher in FIG. 19C than in FIG. 18A. If the correlation falls below a defined level, then the template is discarded. In a further embodiment, a beat validation process may be used to assure that a sensed noisy cardiac event, or simply a noise signal, does not reach the template formation steps, preventing template verification due to the likely low correlation of such a non-validated signal. Some example beat validation processes are shown in co-pending U.S. patent application Ser. No. 10/858,598, filed Jun. 1, 2004, now U.S. Pat. No. 7,248,921, entitled METHOD AND DEVICES FOR PERFORMING CARDIAC WAVEFORM APPRAISAL, and the disclosure of which is incorporated herein by reference.

Figure 19:
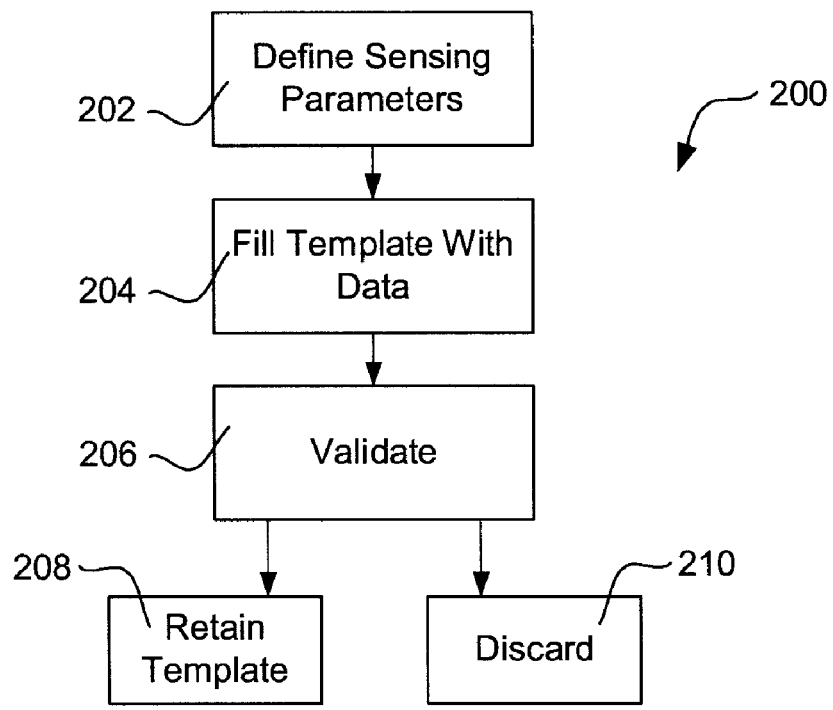
FIG. 19 is a block diagram for an illustrative template formation process.

FIG. 19 is a block diagram for an illustrative template formation process. The process 200 begins by defining a number of sensing parameters, as shown at 202. The sensing parameters may include sampling, window and fiducial point characteristics. Next, a template is filled with data using the sensing parameters, as shown at 204. A validation step follows, as noted at 206. The validation step 206 may include, for example, comparison to successive samples. If validated, the template and its associated sensing parameters are retained as shown at 208. If the template and its associated sensing parameters cannot be validated, then they are discarded as shown at 210.

The present invention, in some embodiments, is also embodied in devices using operational circuitry including select electrical components provided within the canister 12 (FIG. 1A) or canister 32 (FIG. 1B). In such embodiments, the operational circuitry may be configured to enable the above methods to be performed. In some similar embodiments, the present invention may be embodied in readable instruction sets such as a program encoded in machine or controller readable media, wherein the readable instruction sets are provided to enable the operational circuitry to perform the analysis discussed in the above embodiments. Further embodiments may include a controller or microcontroller adapted to read and execute the above methods. These various embodiments may incorporate the illustrative methods shown above, for example.

The following illustrative embodiments are explained in terms of operational circuitry. The operational circuitry may be configured to include such controllers, microcontrollers, logic devices, memory, and the like, as selected, needed, or desired, for performing the method steps of which each is adapted and configured.

The present invention, in an illustrative apparatus embodiment, includes an implantable cardioverter/defibrillator comprising a lead electrode assembly including a number of electrodes, and a canister housing operational circuitry. The illustrative apparatus embodiment may be configured wherein the lead electrode assembly is coupled to the canister, and the operational circuitry is configured to perform steps of discriminating between cardiac rhythms of a patient's heart which are appropriate for therapy, the steps including: sensing a first cardiac event; configuring template parameters for analysis of the first cardiac event; defining a first sensed signal for the first cardiac event using the template parameters; sensing a second cardiac event; defining a second sensed signal for the second cardiac event using the template parameters; and comparing the second sensed signal to the first sensed signal to determine whether the first sensed signal and template parameters are suitable for defining a cardiac event template.

The operational circuitry may, in another embodiment, be configured such that the step of configuring template parameters includes selecting a rule for identifying a fiducial point, and the rule is selected from among a set of rules, the rule is selected in light of the characteristics of the first cardiac event, and the rule for identifying a fiducial point becomes one of the template parameters. In yet another embodiment, the step of configuring template parameters further includes selecting a number of samples of the first sensed signal around the fiducial point, and the configuration of samples around the fiducial point becomes one of the template parameters. In another embodiment, the operational circuitry is configured such that the step of selecting a number of samples includes identifying the start and end of a cardiac event. In on embodiment, the operational circuitry is configured such that the cardiac event is a QRS complex. In some embodiments, the operational circuitry is configured such that the set of rules includes an amplitude rule related to the relative amplitudes of peaks in the sensed signal. The set of rules may include a location rule related to the location of a peak in the sensed signal. In yet another embodiment, the operational circuitry is configured such that the set of rules includes a location rule related to the location of a peak in the sensed signal.

In yet another embodiment, the operational circuitry is configured such that the set of rules includes a notch rule related to identifying a notched cardiac signal, wherein the notch rule includes analysis of whether there are multiple peaks within a predefined range of one another in the cardiac signal. The operational circuitry may be configured such that the notch rule selects the first peak in time if there are multiple peaks within the predefined range. In another embodiment, the operational circuitry may be configured such that the step of configuring template parameters further includes selecting a number of samples of the first sensed signal around a fiducial point in the first sensed signal; wherein the configuration of samples around the fiducial point becomes one of the template parameters. The operational circuitry, in an illustrative embodiment, is configured such that samples are selected using the following steps: first, a number of samples are observed on either side of the fiducial point; next, it is determined whether a desired QRS segment begins and ends within the number of samples; and the number of samples on either side of the fiducial point is adjusted to capture the QRS segment and exclude at least some samples not corresponding to the desired QRS segment. Another illustrative embodiment includes one wherein the operational circuitry is configured such that the step of configuring template parameters includes observing whether a notched QRS complex is likely, and, if so, adjusting the template parameters to assure that a repeatably detectable fiducial point is chosen.

Another embodiment includes an implantable cardioverter/defibrillator comprising a lead electrode assembly including a number of electrodes and a canister housing operational circuitry; wherein: the lead electrode assembly is coupled to the canister; and the operational circuitry is configured to perform steps of discriminating between cardiac rhythms of a patient's heart which are appropriate for therapy. The steps may include sampling a signal using the lead electrode assembly while implanted in a patient's torso in locations chosen for capturing cardiac signals; defining a first sensing window around a first fiducial point to capture a QRS segment; observing the definition of the first sensing window to create template parameters; defining a second sensing window around a second fiducial point using the template parameters; and comparing data in the first sensing window to data in the second sensing window to verify whether to define a valid template using the template parameters. The operational circuitry may be configured such that the step of defining a first sensing window includes identifying a fiducial point by selecting a rule from among a set of rules in light of the characteristics of the QRS segment in the first sensing window, wherein the rule selected for identifying a fiducial point becomes one of the template parameters. Further, the operational circuitry may be configured such that the step defining a first sensing window around a first fiducial point includes identifying the start and end of a cardiac event. If desired, the cardiac event may be a QRS complex.

In another embodiment, the operational circuitry is configured such that the set of rules includes an amplitude rule related to the relative amplitudes of peaks in the sampled signal, and a location rule related to the location of a peak in the sampled signal. In yet another embodiment, the operational circuitry is configured such that the step of defining a first sensing window includes selecting a number of samples around a fiducial point, wherein the configuration of samples around the fiducial point becomes one of the template parameters. The operational circuitry may be configured such that the samples are selected using the following steps: a fiducial point is selected; then a number of samples are observed on either side of the fiducial point; then it is determined whether a desired QRS segment begins and ends within the number of samples; and the number of samples on either side of the fiducial point is adjusted to capture the QRS segment and exclude at least some samples not corresponding to the desired QRS segment.

In yet another embodiment, the operational circuitry is configured such that the step of defining a first sensing window includes observing whether a notched QRS complex is likely, and, if so, adjusting the template parameters to assure that a repeatably detectable fiducial point is chosen.

An illustrative embodiment may include an implantable cardioverter/defibrillator comprising a lead electrode assembly including a number of electrodes and a canister housing operational circuitry, wherein: the lead electrode assembly is coupled to the canister; and the operational circuitry is configured to perform steps of discriminating between cardiac rhythms of a patient's heart which are appropriate for therapy. The steps of discriminating may include forming a template using at least the steps of: sensing a first cardiac event; identifying a first fiducial point in the first cardiac event using a set of rules; sensing a second cardiac event; identifying a second fiducial point in the second cardiac event using the set of rules; determining whether the first fiducial point and second fiducial point were identified using the same rule; and, if not, discarding the first cardiac event.

Another illustrative embodiment includes an implantable cardioverter/defibrillator comprising a lead electrode assembly including a number of electrodes and a canister housing operational circuitry, wherein the lead electrode assembly is coupled to the canister and the operational circuitry is configured to perform steps of discriminating between cardiac rhythms of a patient's heart which are appropriate for therapy. The discriminating steps may include forming a template using at least the steps of receiving a first cardiac signal from the lead electrode assembly, selecting a fiducial point in the first cardiac signal, forming a template around the fiducial point, and verifying the template by receiving additional cardiac signals and using the template to compare the additional cardiac signals to the first cardiac signal. In another embodiment, the operational circuitry is configured such that the step of selecting a fiducial point includes identifying a fiducial point by selecting a rule from among a set of rules in light of the characteristics of first cardiac signal, wherein the rule selected for identifying a fiducial point becomes one of the template parameters. The operational circuitry may be configured such that the step forming a template around the fiducial point includes identifying the start and end of a cardiac event. In another embodiment, the operational circuitry may be configured such that the set of rules includes an amplitude rule related to the relative amplitudes of peaks in the cardiac signal. The set of rules may further include a location rule related to the location of a peak in the cardiac signal. In another embodiment, the operational circuitry is configured such that the set of rules includes a location rule related to the location of a peak in the cardiac signal.

In another embodiment, the operational circuitry is configured such that the step of forming a template includes selecting a number of samples around the fiducial point, wherein the configuration of samples around the fiducial point becomes one of the template parameters. The operational circuitry may be configured such that the samples are selected using the following steps: a number of samples are observed on either side of the fiducial point; it is determined whether a desired QRS segment begins and ends within the number of samples; and the number of samples on either side of the fiducial point is adjusted to capture the QRS segment and exclude at least some samples not corresponding to the desired QRS segment. In yet another embodiment, the operational circuitry is configured such that the step of selecting a fiducial point includes observing whether a notched QRS complex is likely, and, if so, adjusting the template parameters to assure that a repeatably detectable fiducial point is chosen. Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the claims are expressed.

The invention claimed is:

1. A method of generating a template for use in morphology analysis of cardiac activity, as represented by electric signals, in an implantable medical device, the implantable medical device comprising a plurality of implantable electrodes coupled to operational circuitry including at least memory and a controller, the method comprising:
    capturing a cardiac signal using implanted electrodes;
    forming a preliminary template;
    selecting a fiducial point in the preliminary template;
    optimizing the preliminary template; and
    verifying the preliminary template if the preliminary template provides a valid representation of a cardiac event or, otherwise, discarding the preliminary template;
    wherein the step of optimizing the preliminary template comprises masking a portion of the preliminary template by eliminating portions of the preliminary template that do not apparently contain QRS information of the cardiac signal; and
    wherein the step of verifying the preliminary template comprises:
        capturing a cardiac signal and identifying a secondary template;
        selecting a fiducial point in the secondary template in a manner consistent with the step of selecting a fiducial point in the preliminary template, such that both fiducial points are selected in a similar manner;
        optimizing the secondary template in a manner consistent with the step of optimizing the preliminary template; and
        comparing the secondary template to the preliminary template to determine whether the two are sufficiently similar to imply that the preliminary template provides a valid representation of a cardiac event.

2. The method of claim 1 wherein:
    the preliminary template comprises a predetermined number of sequential digital samples of electrical signals captured using the implanted electrodes;
    the step of selecting a fiducial point includes identifying one of the sequential digital samples that represents a peak within the predetermined number of sequential digital samples; and
    the step of optimizing the preliminary template includes:
    identifying QRS start and end points using monotonic signal analysis;
    masking samples outside of the QRS start and end points; and
    retaining samples between the QRS start and end point.

3. The method of claim 2 wherein:
    the optimized preliminary template comprises the fiducial point and a number of retained digital samples on either side of the fiducial point; and
    the step of verifying the preliminary template comprises capturing and configuring a secondary template in accordance with parameters used to optimize the preliminary template.

4. The method of claim 3 wherein the step of configuring the secondary template comprises:
    selecting a fiducial point in the secondary template by identifying a peak corresponding to that identified for the fiducial point of the preliminary template; and
    retaining a number of samples on either side of the fiducial point corresponding to the number of samples retained on either side of the fiducial point of the preliminary template.

5. The method of claim 1 wherein the implantable medical device is an implantable defibrillator, and the method further comprises comparing the verified preliminary template to sensed cardiac events and, if therapy is indicated by a cardiac rhythm, treating the cardiac rhythm.

6. An implantable medical device comprising:
    means for capturing cardiac signals from implanted locations;
    means for performing data analysis; and
    means for data storage in the implantable medical device;
    wherein the means for performing data analysis is configured to perform a method comprising:
    sampling a signal captured using the means for capturing;
    identifying a peak in the sampled signal as a fiducial point;
    configuring a preliminary template using the fiducial point by identifying a number of template samples on either side of the fiducial point, identifying QRS start and end points using monotonic segments on either side of the fiducial point, and masking or discarding portions of the captured cardiac signal falling outside of the identified QRS start and end points;
    testing the preliminary template by comparing it to a similarly configured, later captured cardiac signal, with the comparing step leading to verification of the preliminary template or rejection of the preliminary template; and
    if the preliminary template is verified, storing the preliminary template using the means for data storage.

7. The implantable medical device of claim 6 wherein the means for performing data analysis is configured such that the step of identifying the QRS start and end points comprises identifying the longest monotonic segments occurring before and after the fiducial point.

8. The implantable medical device of claim 6 wherein the means for capturing cardiac signals from implanted locations comprises a plurality of subcutaneous electrodes.

9. The implantable medical device of claim 6 wherein the means for capturing cardiac signals from implanted locations comprises a plurality of implantable electrodes.

10. A method of characterizing a normal sinus rhythm template in an implantable medical device, the implantable medical device comprising a plurality of implantable electrodes coupled to operational circuitry including at least memory and a controller, the method comprising:
    capturing a cardiac signal from implanted electrodes;
    identifying one or more peaks within the captured cardiac signal;
    selecting one of the one or more peaks within the captured cardiac signal as a fiducial point;
    identifying an early monotonic segment occurring prior to the fiducial point;
    identifying a late monotonic segment occurring following the fiducial point;
    defining a preliminary template as including data captured from approximately the beginning of the early monotonic segment to approximately the end of the late monotonic segment, while excluding at least some portion of the captured cardiac signal from the preliminary template;

establishing a configuration for the preliminary template including a duration from the start of the early monotonic segment to the fiducial point and a duration from the fiducial point to the end of the late monotonic segment;

comparing the preliminary template to a number of similarly configured captured cardiac signals to determine whether the preliminary template accurately characterizes normal cardiac function for the patient; and:

if so, storing the preliminary template as a Normal Sinus Rhythm template; or if not, rejecting the preliminary template.

11. The method of claim 10 wherein the step of capturing a cardiac signal includes:

detecting an event from the captured cardiac signal; and certifying the detected event as a cardiac signal.

12. The method of claim 11 wherein the cardiac signal comprises a number of signal samples, and wherein the step of defining a preliminary template includes excluding at least some of the signal samples.

13. The method of claim 10 wherein the implanted electrodes are disposed subcutaneously and not in a heart chamber, in or on the heart muscle, or in a patient's vasculature.

14. A method of cardiac signal analysis comprising:

performing the method of claim 10 until a Normal Sinus Rhythm Template is stored;

capturing a first cardiac signal from the implanted electrodes;

comparing the first cardiac signal to the Normal Sinus Rhythm Template and:

if the first cardiac signal is similar to the Normal Sinus Rhythm Template, determining that the first cardiac signal indicates normal cardiac function; or if the first cardiac signal is not similar the Normal Sinus Rhythm Template, determining that the first cardiac signal does not indicate normal cardiac function.

15. The method of claim 10 wherein the implantable medical device is an implantable defibrillator, and the method further comprises comparing the Normal Sinus Rhythm template to sensed cardiac events and, if therapy is indicated by a cardiac rhythm, treating the cardiac rhythm.

16. A method of establishing a Notched Cardiac Signal Template for a patient having a cardiac rhythm with a QRS complex segment characterized by a notch for use in an implantable cardiac stimulus device comprising a plurality of implantable electrodes coupled to operational circuitry including at least memory and a controller, the notch including first and second peaks separated by a region of lesser amplitude, the method comprising:

determining whether the notch exists by observing whether a captured cardiac preliminary template comprising a plurality of sequential samples of cardiac signal includes first and second peaks that are:

a) separated in amplitude by less than a notch amplitude threshold; or b) separated in time by less than a notch time threshold;

if so, identifying a notched signal and establishing the preliminary template as follows:

selecting the first peak as a fiducial point for the preliminary template;

identifying a QRS width using times associated with the starting time of the largest monotonic segment in the preliminary template preceding the fiducial point and the ending time of the largest monotonic segment in the preliminary template that occurs after the fiducial point; and masking the preliminary template to correspond to the identified QRS width;

then verifying the preliminary template for the notched signal by:

i) capturing at least a detected cardiac event comprising a plurality of sequential samples of cardiac signal;

ii) identifying a fiducial point in the detected cardiac event in the same manner used to identify a fiducial point in the preliminary template;

iii) masking the detected cardiac event around the fiducial point in the same manner used to mask the preliminary template; and iv) comparing the masked detected cardiac event to the masked preliminary template and:

if the detected cardiac event correlates to the preliminary template, determining that the detected cardiac event suggests verification of the preliminary template; or if the detected cardiac event does not correlate to the preliminary template, discarding the preliminary template.

17. The method of claim 16 wherein the step of verifying the preliminary template includes performing steps i)-iv) with up to a predetermined number of detected cardiac events such that:

if analysis of any of the predetermined number of detected cardiac events determines that the preliminary template is not verified, the method includes discarding the preliminary template and identifying a new preliminary template; or if analysis of each of the predetermined number of detected cardiac events suggests verification of the preliminary template, the method includes storing the preliminary template as a verified template for use in subsequent cardiac event analysis.

18. The method of claim 16 wherein the implanted electrodes are disposed subcutaneously and not in a heart chamber, in or on the heart muscle, or in a patient's vasculature.

* * * * *